US008410928B2

(12) United States Patent
Ganguly et al.

(10) Patent No.: US 8,410,928 B2
(45) Date of Patent: Apr. 2, 2013

(54) SYSTEMS AND METHODS FOR EVALUATING CHROMATOGRAPHY COLUMN PERFORMANCE

(75) Inventors: Joydeep Ganguly, Raleigh, NC (US); Jörg Thömmes, San Diego, CA (US)

(73) Assignee: Biogen Idec MA Inc., Cambridge, MA (US)

( * ) Notice: Subject to any disclaimer, the term of this patent is extended or adjusted under 35 U.S.C. 154(b) by 788 days.

(21) Appl. No.: 12/541,014

(22) Filed: Aug. 13, 2009

(65) Prior Publication Data

US 2010/0127860 A1 May 27, 2010

Related U.S. Application Data

(60) Provisional application No. 61/089,351, filed on Aug. 15, 2008.

(51) Int. Cl.
*G08B 21/00* (2006.01)
(52) U.S. Cl. .................. 340/540; 210/198.2; 73/61.53
(58) Field of Classification Search .................. 340/540, 340/500; 210/103, 137, 198.2, 143, 635, 210/656, 659; 73/61.53, 61.56
See application file for complete search history.

(56) References Cited

U.S. PATENT DOCUMENTS

| | | | | |
|---|---|---|---|---|
| 4,840,730 A | * | 6/1989 | Saxena | 210/198.2 |
| 5,417,853 A | * | 5/1995 | Mizuno et al. | 210/198.2 |
| 5,739,422 A | * | 4/1998 | Riviello et al. | 73/61.55 |
| 2002/0182604 A1 | | 12/2002 | Excoffier | |
| 2011/0147312 A1 | | 6/2011 | Cunnien et al. | |

FOREIGN PATENT DOCUMENTS

WO   WO 2009/094203 A2   7/2009

OTHER PUBLICATIONS

Larson, T.M., et al., "Use of process data to assess chromatographic performance in production-scale protein purification columns," *Biotechnology Progress* 19:485-492, American Chemical Society and American Institute of Chemical Engineers (2003).

(Continued)

*Primary Examiner* — Anh V La
(74) *Attorney, Agent, or Firm* — Sterne, Kessler, Goldstein & Fox P.L.L.C.

(57) ABSTRACT

Methods and systems for evaluating and/or monitoring chromatography column performance are provided. Embodiments apply multivariate analysis (MVA) methods to process data as well as transition analysis data to provide a comprehensive evaluation of chromatography column performance. In embodiments, transition analysis data generated over extended periods of time can be analyzed together with process data to evaluate column performance. Further, embodiments enable a compact and robust tool for combining and presenting performance evaluation results, which allows for time-efficient performance examination. According to embodiments, MVA methods applied on transition analysis and process data provide (1) near real-time ability to comprehensively monitor column packing quality; (2) sensitive detection of column integrity breaches; (3) sensitive detection of subtle changes in column packing; (4) sensitive detection of different types of changes in column packing; (5) sensitive detection of fronting/tailing; and (6) sensitive detection of changes in process performance.

14 Claims, 23 Drawing Sheets

OTHER PUBLICATIONS

Ralston, P., et al., "Graphical enhancement to support PCA-based process monitoring and fault diagnosis," *ISA Transactions* 43(4):639-653, The Instrumentation, Systems, and Automation Society (2004).

Stella, C., et al., "Characterization and comparison of the chromatographic performance of different types of reversed-phase stationary phases," *Journal of Pharmaceutical and Biomedical Analysis* 43(1): 89-98 (2007).

Wise, B. M., and N. B. Gallagher, "The process chemometrics approach to process monitoring and fault detection," *J Process Control* 6(6):329-348, Elsevier Publishing (1996).

International Search Report and Written Opinion for International Application No. PCT/US2009/053773, European Patent Office, The Netherlands, mailed on Nov. 20, 2009, 13 pages.

* cited by examiner

| Y | QP1 | | |
|---|---|---|---|
| $R^2$ | 0.76 | | |
| $Q^2$ | 0.73 | | |
| Var ID (Primary) | M10.VIP[2] | | |
| tFrntSlp | 1.16213 | TMAE Elution UV Front Slope |
| tPkHt | 1.14422 | TMAE Elution UV Peak Height |
| tBkSlp10 | 1.13214 | TMAE Elution UV Back Slope (Pk to 10% Pk Height Descending) |
| tVolMid | 1.00968 | TMAE Elution UV Volume Start to Peak Max |
| tVStd10 | 0.961922 | TMAE Elution UV Volume Start to 10% Peak Height Descending |
| tPkWd10 | 0.944189 | TMAE Elution UV Volume @ 10% Peak Height |
| tTailSlp | 0.826636 | TMAE Elution UV Slope 10% Peak Height Descending to End |
| tInfIxVol | 0.734103 | TMAE Elution UV Volume Start to Infection |

FIG. 21

SYSTEMS AND METHODS FOR EVALUATING CHROMATOGRAPHY COLUMN PERFORMANCE

CROSS-REFERENCE TO RELATED APPLICATIONS

This application claims benefit of priority under 35 U.S.C. §119(e) to U.S. Provisional Patent Application No. 61/089,351 filed on Aug. 15, 2008, which is incorporated herein by reference in its entirety.

FIELD OF THE PRESENT INVENTION

The present invention generally relates to chromatography.

BACKGROUND OF THE PRESENT INVENTION

In the biopharmaceutical industry, preparative chromatography using packed-bed columns is a key component in the manufacture of complex biological products (e.g. recombinant proteins & antibodies). Accordingly, it is critical that chromatography column performance is closely monitored and well controlled to ensure high product quality. For example, a high column packing quality is required for efficient chromatographic operations, and deviations from an ideally packed column can result in sub-optimal performance, including increased mobile phase dispersion, poor protein separation, and, potentially, product rejection.

A critical aspect for successful preparative chromatography rests on the ability to implement the best possible methods of process monitoring. Monitoring of chromatography-based processes is typically focused on ensuring that the columns are performing per expectations. Common areas of concern in chromatography using packed-bed columns include, for example: (1) degradation in performance due to column integrity being compromised; (2) degradation due to columns approaching their lifetime limits; (3) equipment malfunction causing problems; and (4) column characteristics changing over time. As such, the function of process monitoring in chromatography processes is one of developing and implementing optimal systems for detecting and addressing inadequate performance or undesirable changes in chromatography procedures.

Today, chromatography process monitoring is performed using a number of methods, such as pulse-input based HETP (Height Equivalent to a Theoretical Plate), monitoring univariate parameters such as asymmetry of a chromatographic peak, elution UV peak width, product yields, and by performing qualitative visual checks of columns and chromatography profiles in attempt to identify anamolies therein.

However, while these methods are useful, they do not provide a sufficiently sensitive and encompassing means for detecting changes or degradation in column performance. Further, in the context of protein purification, it is necessary not only to detect the inherently stochastic behavior associated with the process but also to mitigate the impact of unexpected changes within the columns.

Another problem is that conventional techniques of calculating on-line pulse test HETP are more likely to result in "false positives" which means a packed chromatography column that should have been rejected is, instead, passed. Furthermore, conventional pulse test HETP does not typically reveal gradual trends in column performance. Consequently, by using conventional column chromatography monitoring techniques, valuable product may be run through bad columns and wasted. Conversely, a quality column (which has otherwise shown no adverse trends) may be unnecessarily re-packed when a one time pulse test HETP failure occurs.

Accordingly, there is a need for more quantitative, robust, and less time consuming methods and systems for monitoring and/or evaluating chromatography column performance.

BRIEF SUMMARY OF THE PRESENT INVENTION

This application contains subject matter related to subject matter in U.S. Patent Application No. 61/023,747, filed Jan. 25, 2008 and in International Application PCT/US2009/00469 filed Jan. 23, 2009 each of which are incorporated herein by reference in the entirety.

Methods and systems for evaluating and/or monitoring chromatography column performance are provided.

Embodiments of the invention include applying multivariate analysis (MVA) methods to process data as well as transition analysis data to provide a comprehensive evaluation of chromatography column performance.

In embodiments of the invention, transition analysis data generated over extended periods of time can be analyzed together with process data to evaluate column performance. Further, embodiments of the invention enable a compact and robust tool for combining and presenting performance evaluation results, which allows for time-efficient performance examination.

According to embodiments of the invention, MVA methods applied on transition analysis and process data provide (1) near real-time ability to comprehensively monitor column packing quality; (2) sensitive detection of column integrity breaches; (3) sensitive detection of subtle changes in column packing; (4) sensitive detection of different types of changes in column packing; (5) sensitive detection of fronting/tailing; and (6) sensitive detection of changes in process performance.

Further embodiments of the invention, features, and advantages of the present invention, as well as the structure and operation of various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention and, together with the description, further serve to explain the principles of the present invention and to enable a person skilled in the pertinent art to make and use the present invention.

Figure 18:
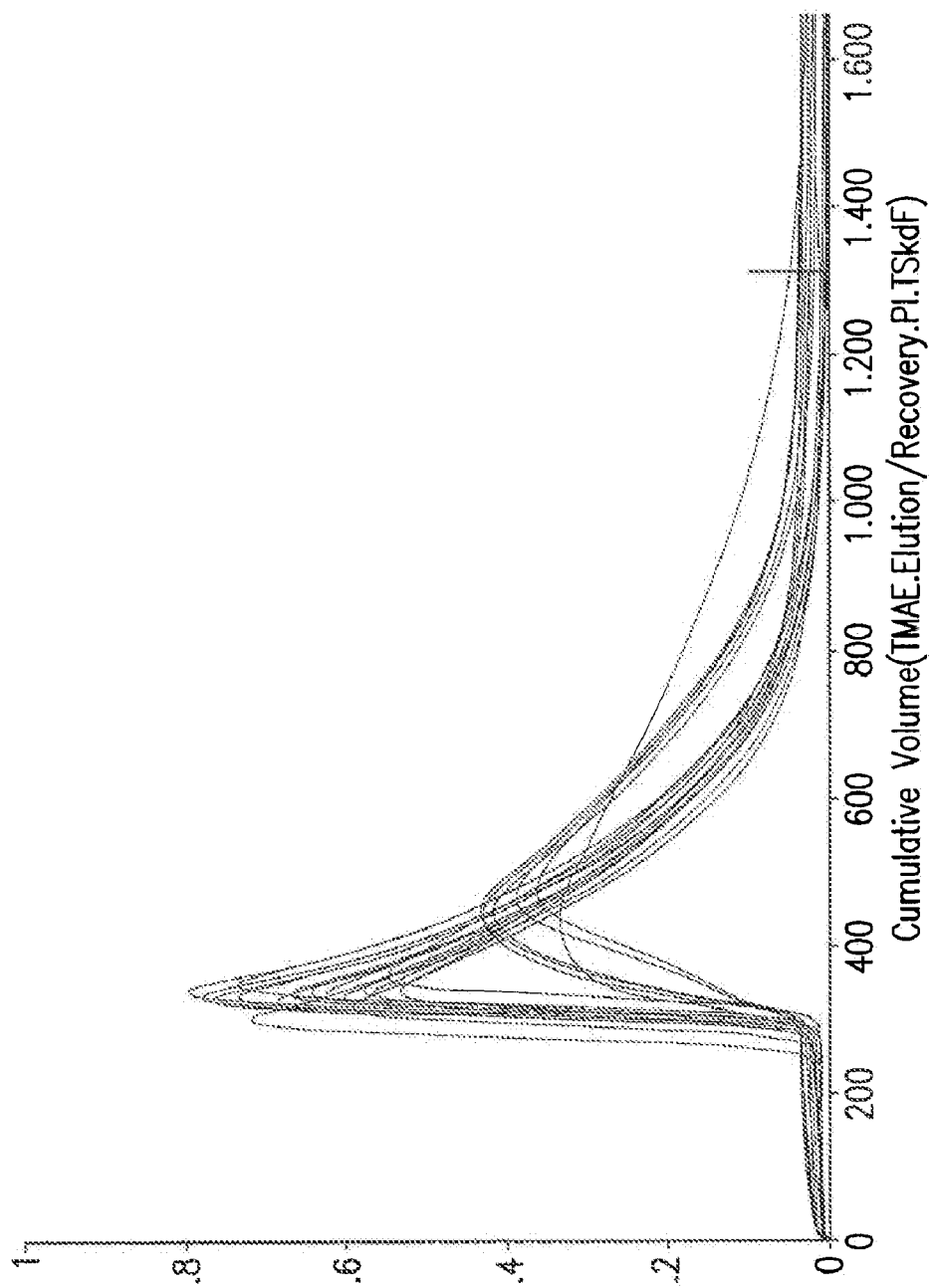

FIG. 18 displays overlayed chromatograms showing differences in elution profiles between historical purification Unit #1 column runs (or batches), purification Unit #2 batches, and Batch 11 from re-packed purification Unit #1 column.

Figure 19:
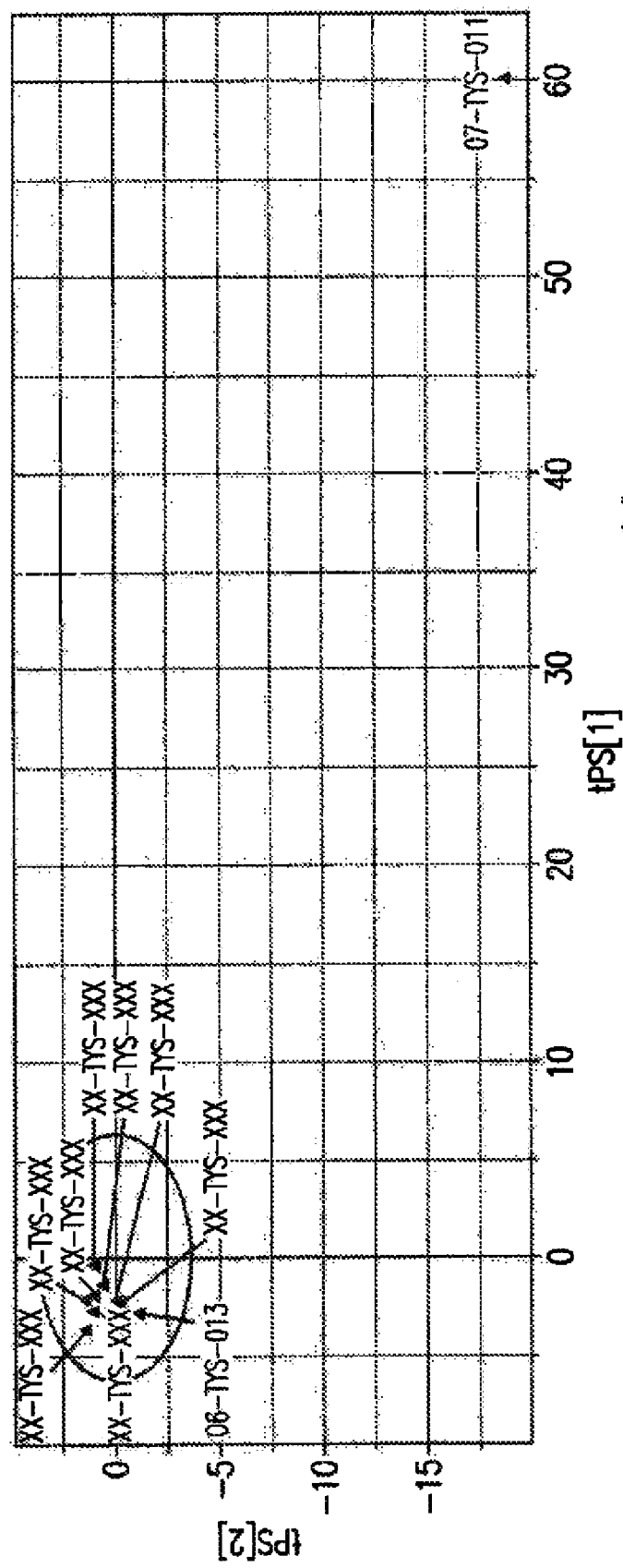

FIG. 19 shows results of multivariate analysis confirming that after the re-pack the TMAE column performance in purification Unit 1 (though different from historical Unit 1 column) was now closer to column performance in purification Unit 2.

Figure 20:
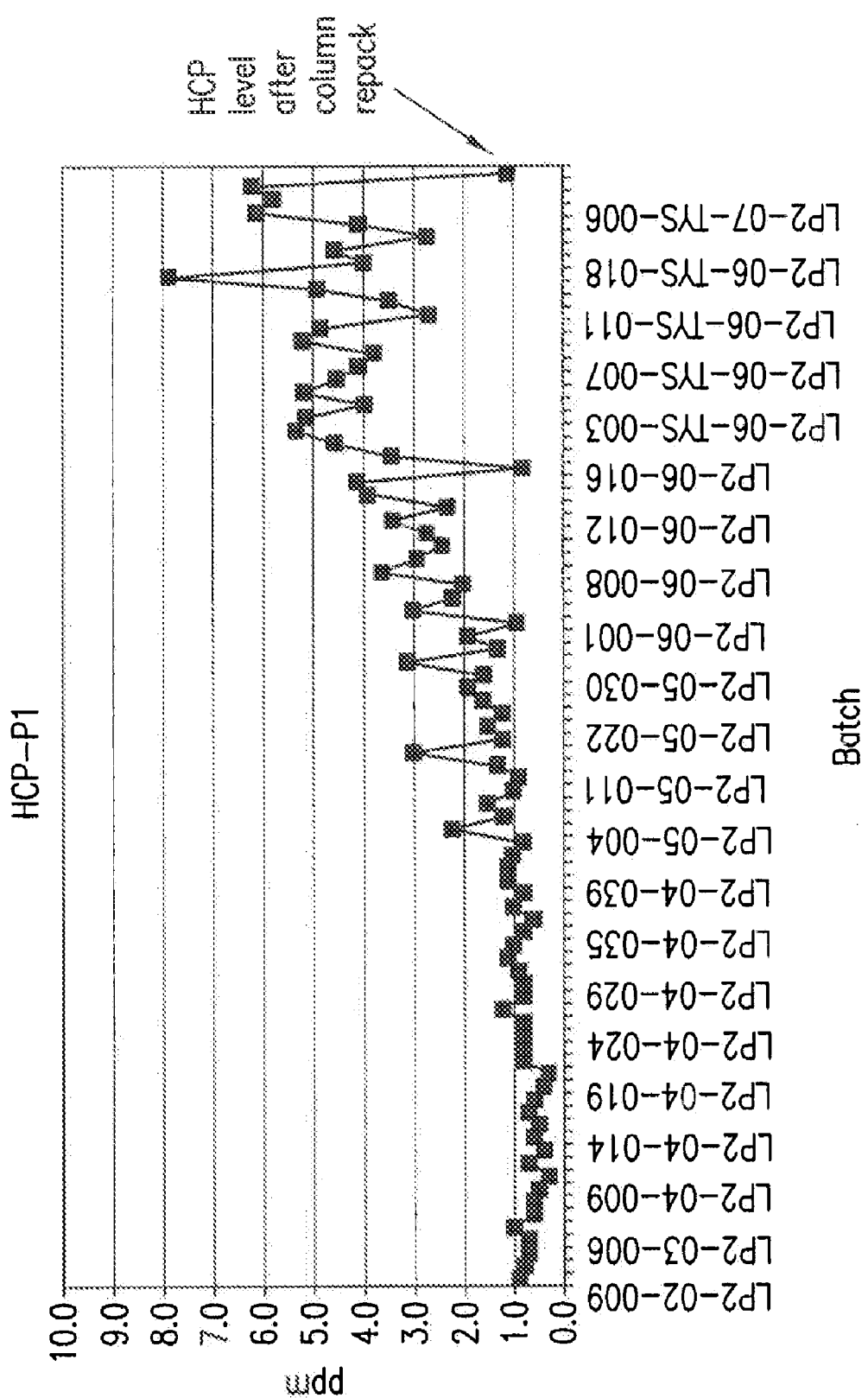

FIG. 20 shows relative level of HCP after column re-pack (last data point) versus trend toward increased HCP levels (all data points preceding the last).

FIG. 21 shows the resulting parameter set derived for a model in which 8 important parameters for predicting levels of contaminating host cell protein during an anion exchange chromatography were identified; a model of excellent fit and predictability was obtained as evidenced by R2 and Q2 values of 0.76 and 0.73, respectively.

Figure 22:
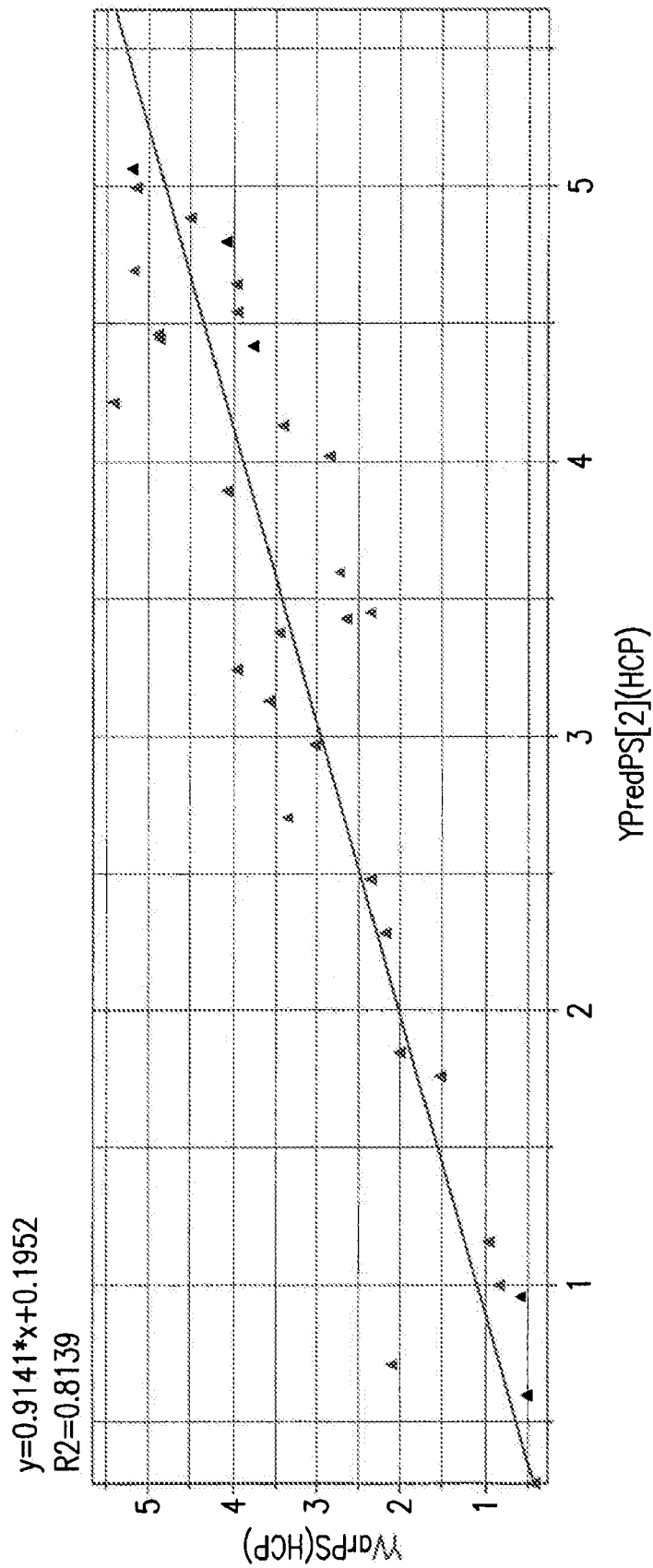

FIG. 22 shows the excellent correlation between measured and predicted Host Cell Protein contaminant concentrations in a purified Drug Substance following Anion Exchange Chromatography procedures.

Figure 23:
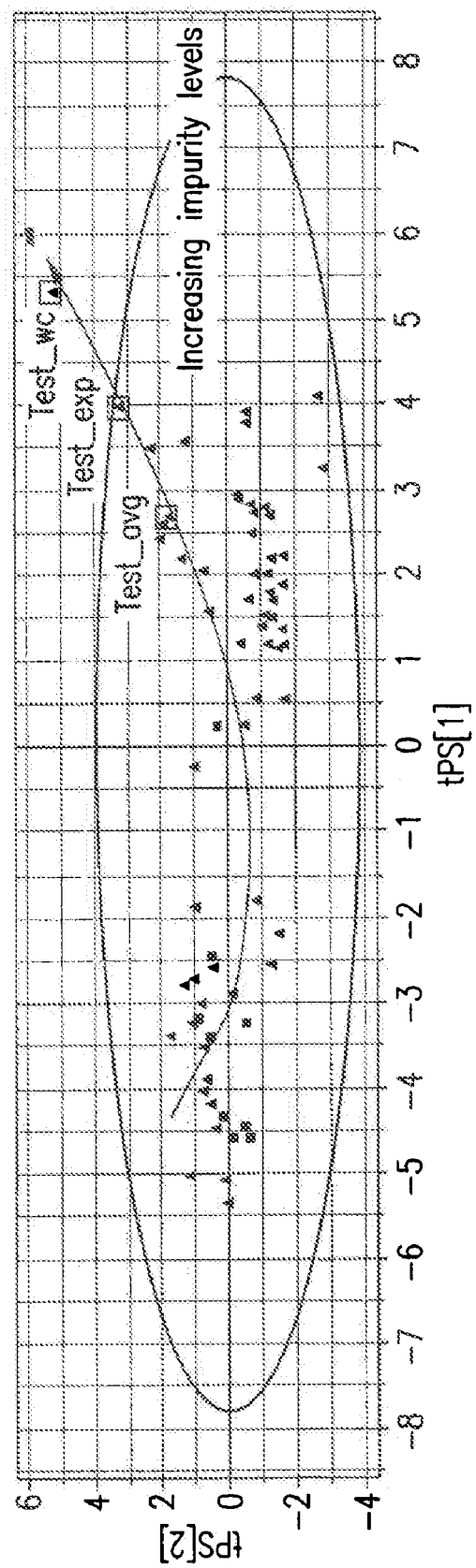

FIG. 23 shows a PCA plot of a resulting multivariate analytical model. The ellipsoid represents the 95% confidence interval, while the curved arrow indicates how a predicted and measured impurity concentration trends with repeated use of hydrophobic interaction chromatography media.

The present invention is described with reference to the accompanying drawings. The drawing in which an element first appears is typically indicated by the leftmost digit or digits in the corresponding reference number.

DETAILED DESCRIPTION OF THE PRESENT INVENTION

Methods and systems for evaluating and/or monitoring chromatography column performance are provided herein. In the detailed description of the present invention that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

In preparative column chromatography, a well-packed bed of resin is required for achieving optimal separation and purification results. Variations from that of an ideally packed bed result in sub-optimal performance, including, for example, increased mobile phase dispersion, poor protein separation and, possibly, product rejection. Regardless of type, the best strategy for optimizing chromatography performance includes implementing the best possible system for analyzing and monitoring column performance.

Recent advances in monitoring include measuring chromatographic bed integrity through algorithms applied to Transition Analysis. This has greatly facilitated mathematical analysis of bed integrity, particularly statistical moment-based calculation of height equivalent to a theoretical plate (HETP). This method does not assume ideal conditions and calculates a true HETP, which is a measure of bed integrity. The most common approach in these more recent efforts has been to transform a breakthrough or washout curve into a peak by taking the first derivative. The dispersion parameters are then derived from the peak position and shape. Transition Analysis is the inference of dispersion parameters from a step transition. A step transition is an abrupt change in the mobile phase, preferably reflected by a change in a measurable physical characteristic in the fluid, e.g. conductivity, pH, protein concentration, etc. In preparative chromatography, a step transition is either in the form of a breakthrough curve or a washout curve.

While transition analysis provides a useful tool in assessing column bed integrity, and product yield provides a useful tool in assessing process performance in a batch, the volume of information that must be processed to assess slow and gradual degradation of columns is not captured by simply viewing isolated parameters within a batch. In addition, subtle changes that occur in the process may not be identified by viewing univariate transition analysis parameters. In contrast, assessing multivariate combinations of data via an algorithm or algorithms for processing such data may reveal otherwise unidentified undesirable deviations in column bed integrity and/or process performance.

A method of processing multivariate information in a context allowing seamless batch-to-batch comparison, and then allowing the user to quantitatively determine excursions from past batches presents users with a powerful analytical capability. Hence, embodiments of the present invention include an analytical "toolbox" for achieving enhanced analytical capability of column chromatography process performance. Embodiments of the invention are based on empirical examples using a combination of conventional multivariate methods (such as for example, but without limitation, PCA and PLS) as well as classical statistical process control charts.

Principal Component Analysis (PCA) is a Multivariate Statistical Method where a data set containing many variables is reduced to a few variables called Scores (t). The Components or t-Scores contain information about the variation of each variable in the data set and the correlation of each variable to every other variable in the data set. As such, t-Scores describe the variation and correlation structure of each Observation or Batch in the data set compared to other Observations or Batches in the data set. The PCA plot is a commonly used graphic output of PCA. The PCA plot is a plot of one Component (t-Score) against another Component, usually t1 vs. t2. The PCA plot is essentially a distribution, which shows how the variation and correlation structure compare for all of the Observations or Batches in the data set.

Partial least squares (PLS) regression (path) analysis is a multivariate regression technique for analysis of systems of independent and response variables. PLS is a predictive technique which can handle many independent variables, even when these display multicollinearity. PLS can also relate the set of independent variables to a set of multiple dependent (response) variable. In PLS typically, one set of latent variables is extracted for the set of manifest independents and another set of latent variables is extracted simultaneously for the set of manifest response (dependent) variables. The extraction process is based on decomposition of a cross-product matrix involving both the independent and response variables. The X-scores of the independent latents are used to predict the Y-scores or the response latent(s), and the predicted Y scores are used to predict the manifest response variables. The X- and Y-scores are selected by PLS so that the relationship of successive pairs of X and Y scores is as strong as possible. The advantages of PLS include ability to model multiple dependents as well as multiple independents; ability to handle multicollinearity among the independents; robustness in the face of data noise and (depending on software used) missing data; and creating independent latents directly on the basis of cross-products involving the response variable(s), making for stronger predictions.

The advantage of representing many variables in one plot like the PCA plot is that it provides an easier method for displaying differences between observations, while at the same time allowing users to "drill down" into the potential cause of the variation between observations. Thus, by taking into account multivariate interactions between different parameters, this application allows for easier detection of atypical behavior and aids in highlighting undesirable trends. Examples, without limitation, of just a few parameters that may be monitored as part of a multivariate analytical assessment include changes in: protein concentration (or titer); protein isoforms (e.g., varying pI); impurity levels of compounds with higher or lower molecular weight than the target product; biological activity; relative potency; post-translational modifications (e.g., carbohydrate modification such as glycosylation/galactosylation); host cell protein content; product aggregation; half-antibody content; proteolysis; osmolality; pH; leaching of column components; etc.

In an embodiment of the present invention, an analytical "toolbox" for multivariate chromatography process monitoring may comprise:

An online system providing the ability to overlay chromatograms, one on top of another. Such a system permits use of pattern recognition methods to isolate differences in column performance (which may impact process performance). The ability to compare multiple chromatograms to a "gold" or ideal standard, provides users with enhanced abilities to detect atypical column behavior during a process "run." In addition, comparison and assessment of analytics such as slopes of rise in chromatography curves (e.g., during elution, wash, etc.) provides a quantitative means for evaluating chromatograms, thereby reducing operator subjectivity in assessing the performance of a given column in a batch.

A system wherein Transition Analysis parameters are computed for particular transitions in a process, thereby providing univariate transition analysis parameters that may be used to detect bed integrity issues instantly.

A multivariate model graphically depicting the distribution of observations in a process, in relation to each other, using each of the observed parameters in a process (including Transition Analysis outputs, product yields, cycle numbers, etc). For example, using PCA techniques multivariate parameters may be used to construct a model graphically displaying variation between observations and allowing for gap analysis to be readily conducted.

As such, these three tools, when combined into a consolidated data analytics package, provide the ability to, for example, but without limitation: (1) monitor and detect bed integrity issues in near real-time and with increased sensitivity; (2) detect slow, gradual and/or subtle changes in column packing and performance; (3) determine optimal column lifetimes; (4) remove subjectivity in evaluating chromatograms and process performance; (5) provide increased sensitivity to a variety of different types of changes or failures in optimal column packing and performance (e.g., voids, channeling, air bubbles, clogging); and, (6) provide increased sensitivity to fronting/tailing.

Thus, while various monitoring measures (Transition Analysis HETP, yield, and visual monitoring of chromatograms) are useful, when viewed in isolation (i.e., as univariate parameters) such methods do not provide optimal sensitivity and ability to detect changes or gradual degradation in column performance. In contrast, synergistic value can be achieved when applying use of these univariate tools in a multivariate fashion. Accordingly, embodiments of the present invention are demonstrated through application of empirical examples to show that applying multivariate methods of collecting, presenting, and trending column chromatography parameters provides significantly more powerful and robust methods of measuring and monitoring column integrity and performance. Moreover, the methods described herein have a variety of applications, such as for example: in determining or predicting when column re-packing, regeneration, or disposal should be performed; in identifying and rectifying causes and conditions of sub-optimal process performance; and, in developing an ideal model of process performance parameters falling within an acceptable range of numerous process parameter averages.

Figure 1:
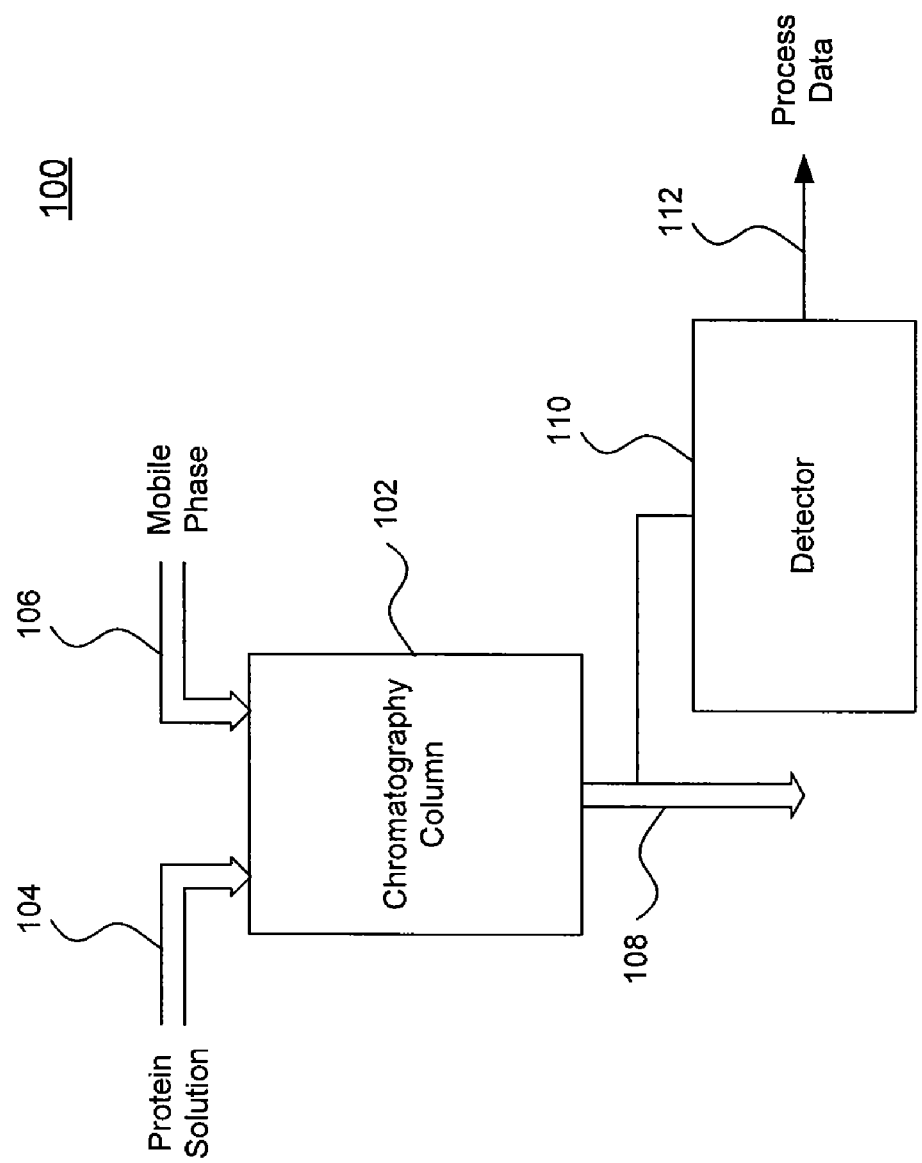
FIG. 1 is a diagram that illustrates an example process chromatography system.

FIG. 1 is a diagram that illustrates an example process chromatography system 100. System 100 may be used to separate bio-molecules in a complex mixture, isolate a single bio-molecule, and/or eliminate contaminants. As shown in FIG. 1, system 100 includes a chromatography column 102 and a detector 110.

Chromatography column 102 is filled with a permeable, semi-permeable, or impermeable solid matrix immersed in a mobile phase. Generally, a protein solution 104 is applied at the top of chromatography column 104. Then, a mobile phase 106 is continuously pumped through chromatography column 102. Since different proteins in protein mixture 102 interact differently with the solid matrix in chromatography column 102, they can be collected separately at the output 108 of chromatography column 102.

Detector 110 is coupled to the output 108 of chromatography column 102. Accordingly, detector 110 monitors the flow out of chromatography column 102 and generates process data 112. Process data 112 includes data that can be used to infer information regarding the performance of chromatography column 102, including process parameters.

For example, process data 112 typically includes outflow information such as step yields, which provide an indicator of process performance within a batch of mobile phase. In embodiments of the invention, detector 110 can be any type of detector that is capable of monitoring process properties relating to the efficiency and/or packing quality of chromatography column 102. For example but without limitation, detector 110 may be an electrical conductivity detector, an ultraviolet (UV) detector, a fluorescence detector, a refractive detector, or a pH detector.

Figure 2:
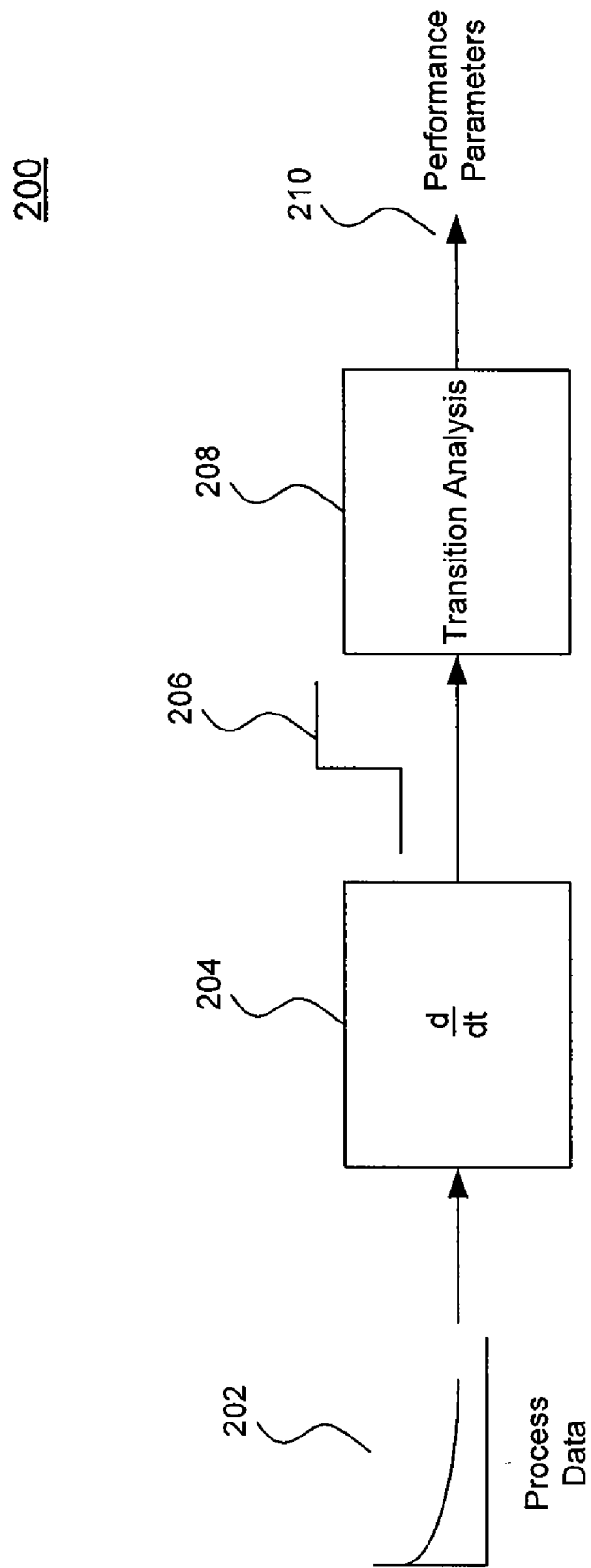
FIG. 2 is a diagram that illustrates an example process for evaluating chromatography column performance.

FIG. 2 is a diagram that illustrates an example process 200 for evaluating chromatography column performance. In particular, process 200 illustrates the inference of additional performance parameters 210 from process data 202.

As described above in FIG. 1, process data 202 can be generated by a detector coupled to the output of a chromatography column. Process data 202 includes step yields and measurements of other mobile phase parameters, which can be in the form of a breakthrough or washout curve that corresponds to a chromatography step transition. As used herein, a chromatography step transition is a relatively abrupt change in the mobile phase in a chromatography column that is reflected by a change in a measurable physical characteristic such as, for example and without limitation: conductivity; pH; salt concentration; light absorption; fluorescence after excitation with light of a suitable wavelength; refractive index; electrochemical response; and, data generated by mass spectrometric analysis.

A step transition is typically due to the replacement of one mobile phase liquid (e.g., solution) by another mobile phase liquid (solution) in a continuously flowing manner. Generally, a step transition can be thought of as having three phases (e.g., a baseline phase, a transition phase, and a saturation or plateau phase), and is different than a pulse or a gradient.

Example process 200 begins in step 204, which includes processing process data 202 to generate a curve 206. Typically, step 204 includes taking the first derivative of a breakthrough or washout curve to generate curve 206. Generally, curve 206 is characterized by a peak, which can be analyzed based on shape and position to infer further information about the performance of the chromatography column.

As such, subsequently, in step 208, process 200 includes analyzing curve 206 to generate performance parameters 210. In particular, step 208 includes performing transition analysis on curve 206 to generate performance parameters 210. Performance parameters 210 generated through transition analysis include, for example, dispersion parameters.

Process data analysis, as described above with reference to FIG. 2, provides a useful tool for information about process performance within a mobile phase batch. Transition analysis, as described above with reference to FIG. 3, provides an excellent tool for information regarding column integrity within a batch. However, neither type of analysis in isolation is capable of capturing the slow, progressive, and gradual degradation of columns over time (generally occurring over several batches). In addition, since transition analysis is based on a univariate examination of step transition data, it is often the case that transition analysis data (i.e., transition analysis performance parameters) does not capture subtle changes in the process.

Embodiments of the present invention address the above deficiencies of process data analysis and transition analysis. In particular, embodiments of the invention apply multivariate analysis (MVA) methods to process as well as transition analysis data to provide a comprehensive evaluation of chromatography column performance.

In embodiments of the invention, transition analysis data generated over extended periods of time can be analyzed together with process data to evaluate column performance. Further, embodiments of the invention enable a compact and robust tool for combining and presenting performance evaluation results, which allows for time-efficient performance examination.

In an embodiment of the invention transition analysis data and/or process data is transformed (e.g., by filtering and/or by smoothing) to form transformed values in which noise present in the values is suppressed. Column performance parameters are calculated based on the transformed values. Thus, embodiments of the invention, comprise: 1) filtering a plurality of process and/or transition analysis values; (2) smoothing a plurality of process and/or transition values; and, 3) calculating moving averages for the plurality of process and/or transition analysis values.

According to embodiments of the invention, MVA methods applied on transition analysis and process data provide (1) near real-time ability to comprehensively monitor column packing quality; (2) sensitive detection of changes in column integrity; (3) sensitive detection of subtle changes in column packing; (4) sensitive detection of different types of changes in column packing; (5) sensitive detection of fronting/tailing; and (6) sensitive detection of changes in process performance. Some exemplary column chromatography problems include, without limitation, sample overloading, clogging, voids, channeling and air bubbles in the mobile phase.

Figure 3:
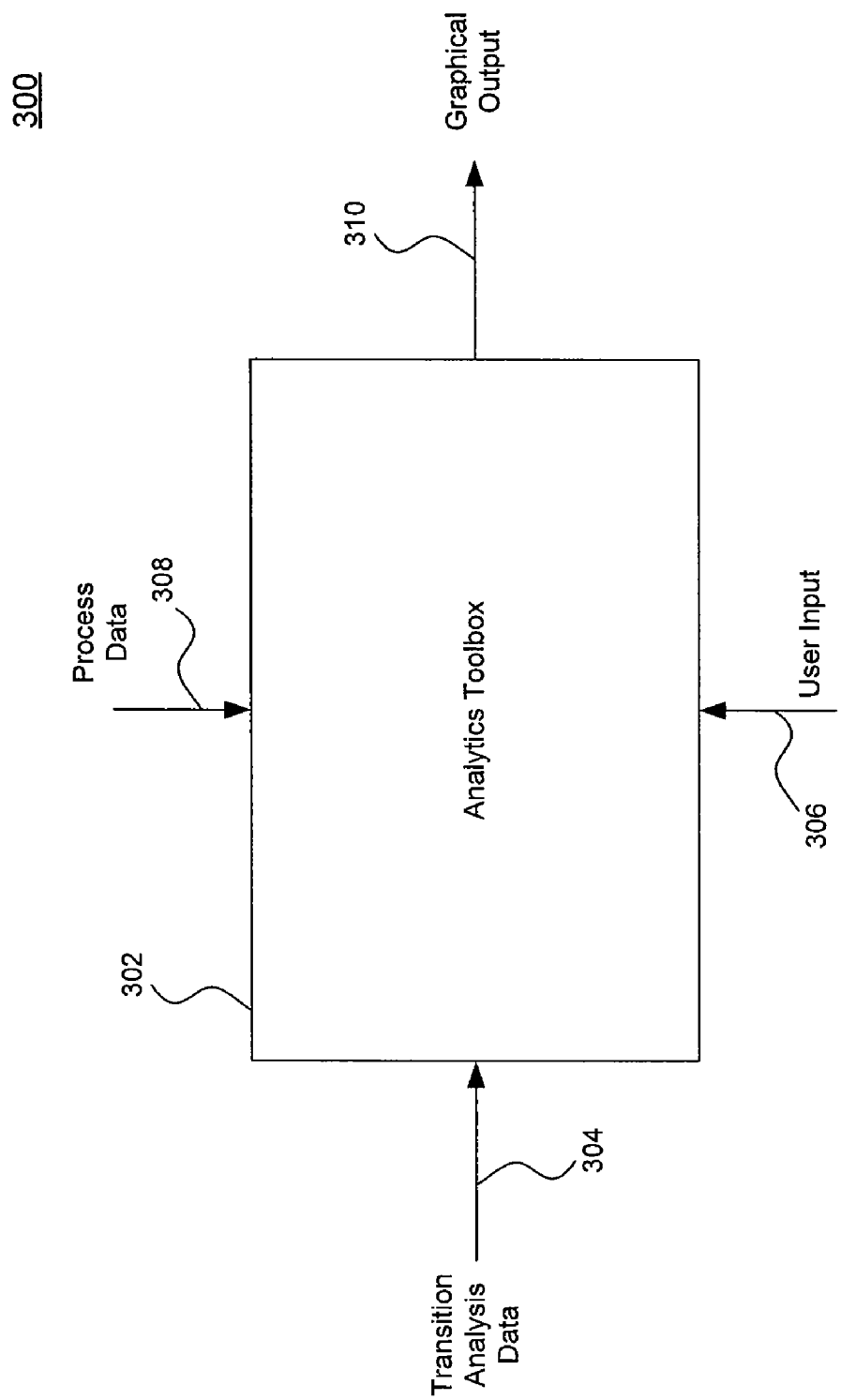
FIG. 3 is a diagram that illustrates an example system for evaluating chromatography column performance according to an embodiment of the present invention.

FIG. 3 is a diagram that illustrates an example system 300 for evaluating chromatography column performance according to an embodiment of the present invention. As shown in FIG. 3, example system 300 includes an analytics toolbox 302. Analytics toolbox 302 receives process data 308, transition analysis data 304, and user input 306, and generates a graphical output 310 representative of the performance of a chromatography column.

In an embodiment of the invention, system 300 is coupled to a detector such as detector 110 described above with reference to FIG. 1. The detector provides analytics toolbox 302 with process data 308, generated as a result of monitoring a chromatography column. For example, the detector provides analytics toolbox 302 process data in the form of process parameters.

In an embodiment of the invention, system 300 is coupled to a transition analysis module capable of generating transition analysis data. The transition analysis module performs a process such as process 200 described above with reference to FIG. 2, and provides system 300 with transition analysis data 304. For example, the transition analysis module provides analytics toolbox 302 with transition analysis data in the form of transition analysis parameters.

In an embodiment of the invention, system 300 is coupled to a user interface for receiving user input 306. User input 306 may include input to indicate the type of analysis to be performed, the particular performance parameters to be examined, as well as the type of graphical representation to be used for the performance results to be presented.

In an embodiment of the invention, analytics toolbox 302 generates graphical output 310 based on process data 308, transition analysis data 304, and user input 306.

Figure 4:
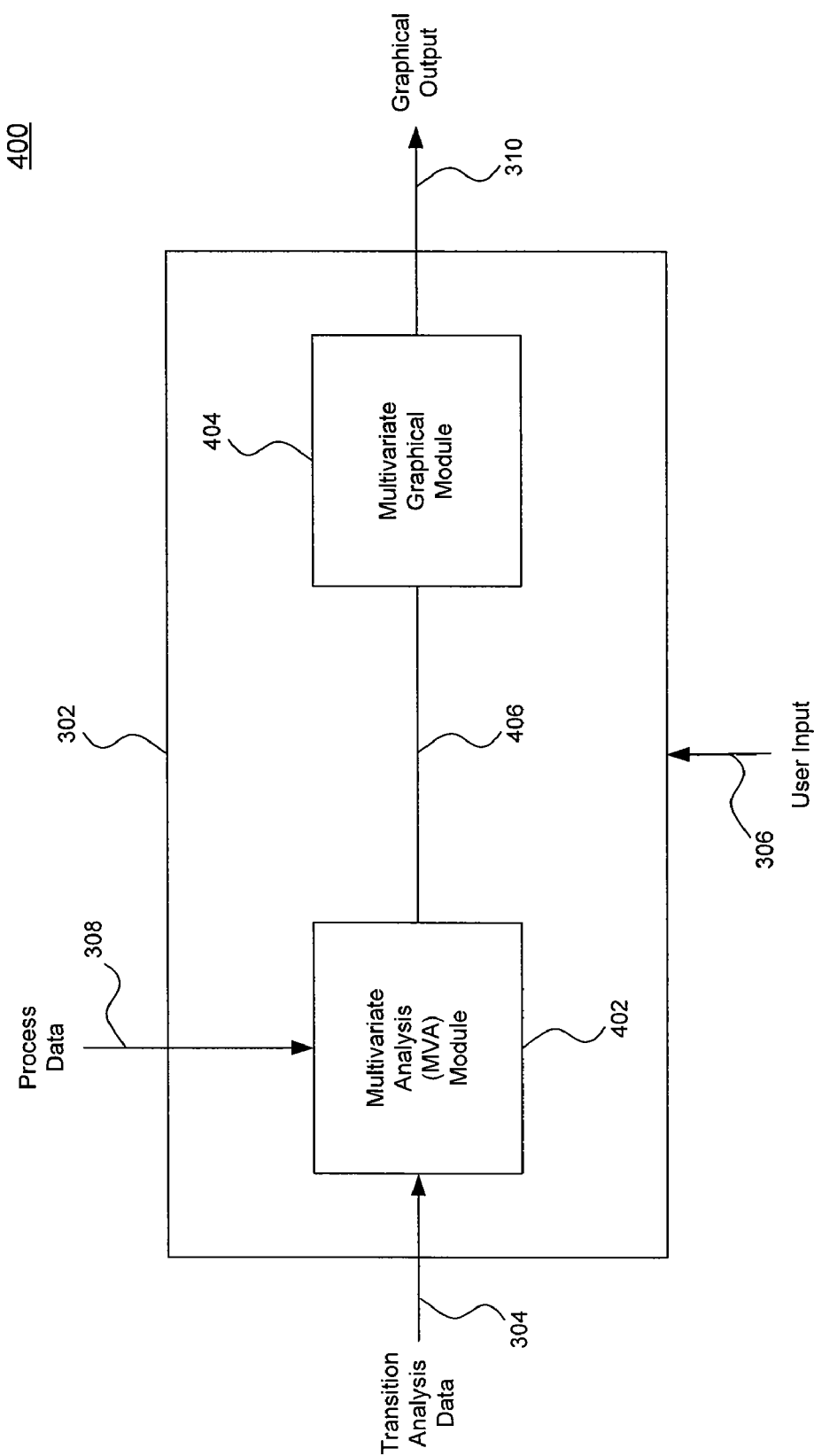
FIG. 4 is a diagram that illustrates an example system for evaluating chromatography column performance according to an embodiment of the present invention.

In an embodiment of the invention, as illustrated in embodiment 400 of FIG. 4, for example, analytics toolbox 302 includes a multivariate analysis (MVA) module 402 and a multivariate graphical module 404.

As shown in FIG. 4, MVA module 402 receives process data 308 and transition analysis data 304, and generates a performance evaluation output 406. In an embodiment of the invention, performance evaluation output 406 is generated by applying MVA methods on process data 308 and transition analysis data 304. It is noted that MVA methods generally encompass univariate analysis methods. As such, analytics toolbox 302 enables process performance evaluation that is inferred from process parameters and detection of column integrity issues that is generally enabled by transition analysis parameters.

Multivariate graphical module 404 receives performance evaluation output 406 from MVA module 402 and generates a graphical output 310 therefrom. In an embodiment of the invention, graphical output 404 is adapted according to user input 306 and may include a variety of graphical representation options, including for example but without limitation, charts, histograms, plots, etc.

In an embodiment of the invention, graphical module 404 operates based on a model, which is constructed a priori based on a list of parameters that are of interest in the purification process.

In an embodiment of the invention, multivariate graphical module 404 enables graphical illustration of process observation distributions. In an embodiment of the invention, the graphical illustration encompasses all parameters in the process, including for example transition analysis data, process data, yields, cycle numbers, etc. In another embodiment of the invention, graphical module 404 enables graphical display of observation variations and allows for gap analysis to be readily performed.

Figure 5:
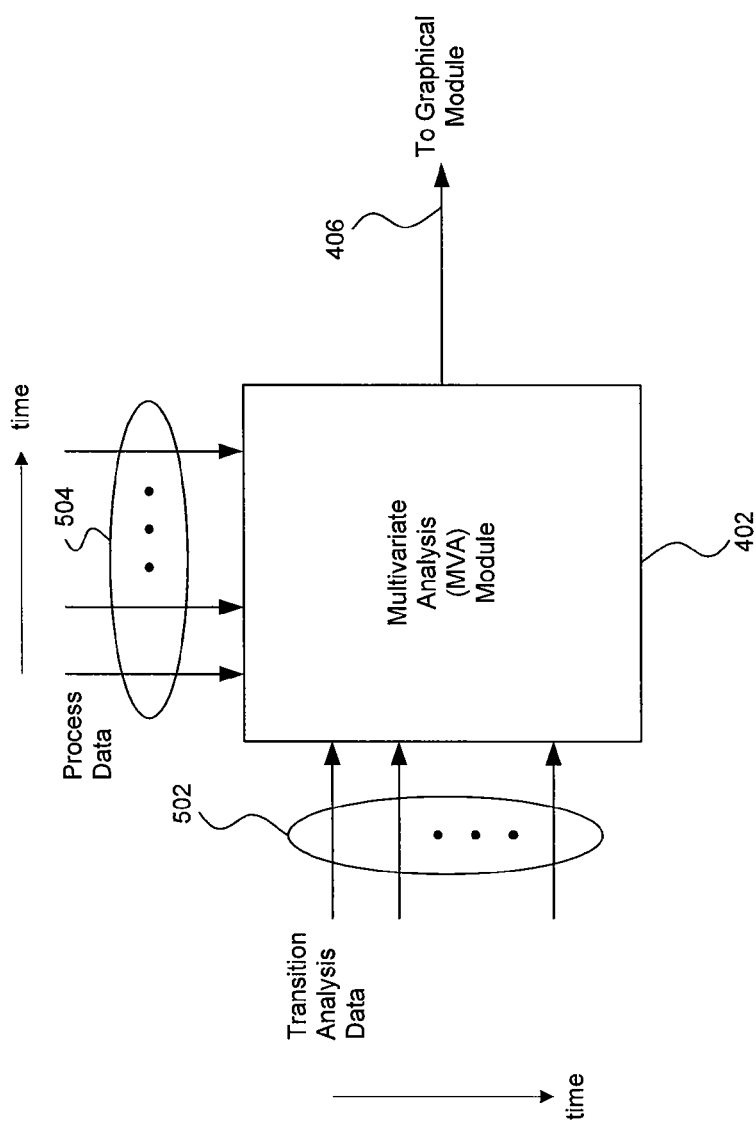
FIG. 5 is a diagram that illustrates an example multivariate analysis module for evaluating chromatography column performance according to an embodiment of the present invention.

FIG. 5 is a diagram that illustrates an example embodiment 500 of MVA module 402 according to an embodiment of the present invention. In particular, example embodiment 500 illustrates the ability of MVA module 402 to process multiple data sets corresponding to respective time instants in the lifetime of a chromatography column. As such, performance evaluation results generated by MVA module 402 can provide indication of slow, subtle, progressive changes in column performance.

As shown in FIG. 5, MVA module 402 receives multiple sets of transition analysis data 502 and process data 504. These sets can be received by MVA module 402 all at once or in real-time as they are generated.

In an embodiment of the invention, the received data 502 and 504 include a plurality of chromatograms that correspond to respective outputs, in time, of a chromatography column. In an embodiment, MVA module 402 provides the ability to overlay chromatograms and allows for pattern recognition methods to be used to isolate differences in column performance over time. Further, MVA module 402 provides the ability to compare multiple chromatograms to a "gold standard", which makes in-process detection of atypical column behavior significantly easier. In addition, MVA module 402 provides quantitative analytical methods (e.g., slope of rise) which can be applied to chromatography curves (e.g., elution, wash, etc.), thus providing an objective approach for an operator to evaluate the performance of the column in a batch.

Figure 6:
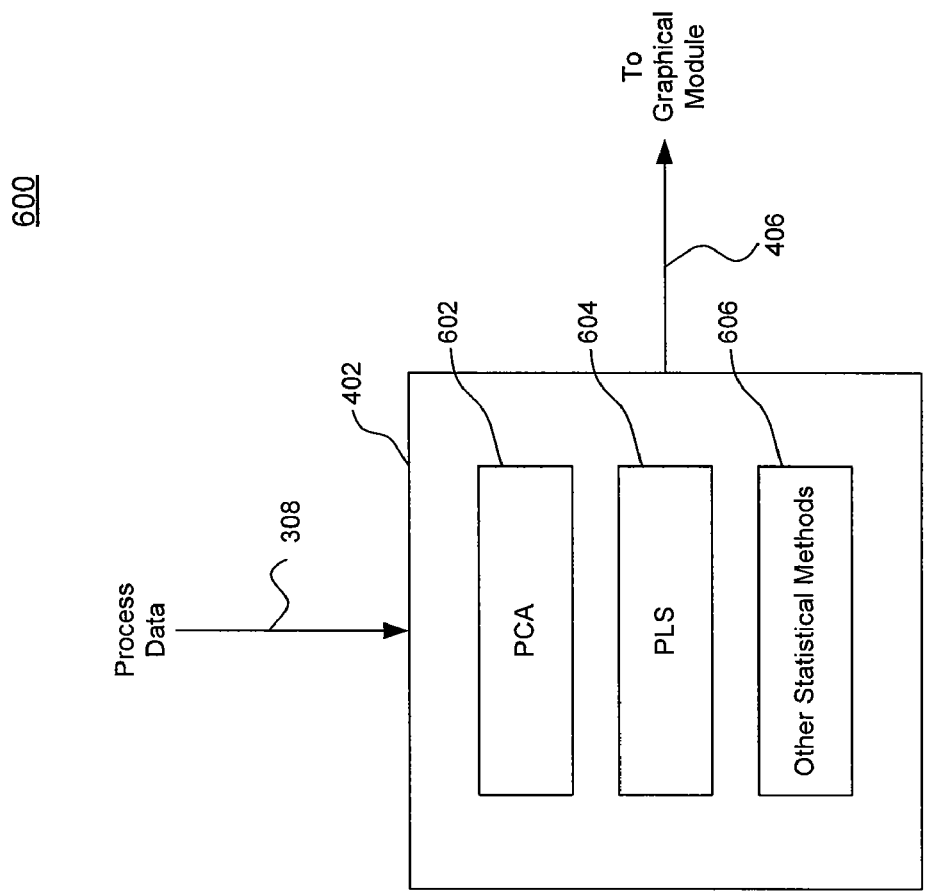
FIG. 6 is a diagram that illustrates an example multivariate analysis module for evaluating chromatography column performance according to an embodiment of the present invention.

FIG. 6 is a diagram that illustrates another example embodiment 600 of MVA module 402 according to an embodiment of the present invention. In particular, example embodiment 600 illustrates some different possible data analysis methods of MVA module 402, which include, for example, Principal Component Analysis (PCA) methods 602, Partial Least Squares (PLS) regression methods 604, as well as other conventional statistical data analysis methods 606.

Principal Component Analysis (PCA) is a multivariate statistical analysis method, in which a multi-dimensional data set is reduced to lower dimensions for analysis. The results of a PCA are generally called components or t-Scores. Components or t-Scores contain information about the variation of each variable in the data set as well as its correlation with every other variable in the data set.

According to embodiments of the present invention, when PCA is applied to a data set including multiple observations from a chromatography column, the resulting t-Scores create a correlation matrix that describes variations within and between the multiple observations. As such, the correlation matrix includes information that describes variation within each observation or batch in the data set (auto-correlation information) and information that describes variation between any two observations or batches in the data set (cross-correlation information).

The PCA plot is a commonly used graphical output of PCA. The PCA plot is a plot of one component or t-Score against another. According to embodiments of the present invention, multivariate graphical module 404 can be used to display PCA plots according to PCA results generated by MVA module 402. It is noted that one advantage of representing many components/variables into one plot such as a PCA plot is that it provides an efficient way of quantitatively displaying differences between observations, while at the same time allowing a user to "drill down" into potential causes of variation between observations.

Partial Least Squares (PLS) regression analysis is a multivariate regression technique for analysis of systems of independent and dependent (response) variables. PLS is a predictive technique which can be used to process multiple independent variables, even when the variables display multicollinearity. Generally, PLS operates by relating the set of independent variables to a set of multiple response variables. Then, one set of independent latent variables is extracted for the set of (manifest) independent variables, and another set of response latent variables is extracted simultaneously for the set of (manifest) response variables. The extraction process is based on the decomposition of a cross-product matrix involving both the independent and response variables. Subsequently, X-scores of the independent latent variables are used to predict Y-scores or the response latent variables, and the predicted Y-scores are used to predict the manifest response variables. The X- and Y-scores are selected by PLS so that the relationship of successive pairs of X and Y scores is as strong as possible.

Advantages of PLS include the ability to model multiple dependent variables as well as multiple independent variables; the ability to handle multi-collinearity among the independent variables; robustness in the face of data noise and (depending on software used) data loss; and creating independent latent variables directly on the basis of cross-products involving the response variable(s), making for stronger predictions.

According to embodiments of the present invention, data analysis methods used by MVA module 402 rely on a hierarchical model which allows for large amounts of chromatography data to be processed and represented in a consolidated manner in real time. This is one advantage of embodiments of the present invention over conventional analysis methods, which main weaknesses include the inability/inefficiency to process large amounts of information. For example, transition analysis modules return 8 parameters per phase per column for a typical four-column, four-phase operation. This results in 128 parameters per batch that can be processed. Conventional analysis methods use a combination of pre-defined alarm limits and/or univariate analysis methods to isolate differences between observations and detect potential atypical behavior. However, conventional methods fail to fully and/or efficiently utilize all the information that is available. For instance, from one extreme, alarm limits only indicate discrete excursions from action limits and give minimal or no information about undesirable trends in the data. From another extreme, univariate analysis methods can generate large amounts of information which overwhelm the user and take excessive amounts of time to process.

Hence, the hierarchical model (an embodiment of the present invention) solves the above-mentioned deficiency by using a "layered" or "parent" PCA plot, which allows for large numbers of parameters in a batch to be monitored and effectively presented in a single plot (or a small number of plots, depending on user preferences). Embodiments of the invention include use of the hierarchical analytical model described herein, wherein the number of parameters monitored in a batch may be equal to or greater than about 10, 20, 30, 40, 50, 60, 70, 80, 90, 100, 150, 200, 250, 300, 350, 400, 450, 500, 600, 700, 800, 900, 1000 or more.

In an embodiment of the invention, constructing the parent PCA plot includes constructing sub-model PCA plots at a unit operation level (e.g., in an embodiment, a PCA plot is generated for each column with data for each univariate parameter included) and then weighting the sub-model PCA plots to generate the parent PCA plot. As such, the parent PCA plot uses the sub-models as variables and allows for observations to be compared on a sub-model basis.

Figure 7:
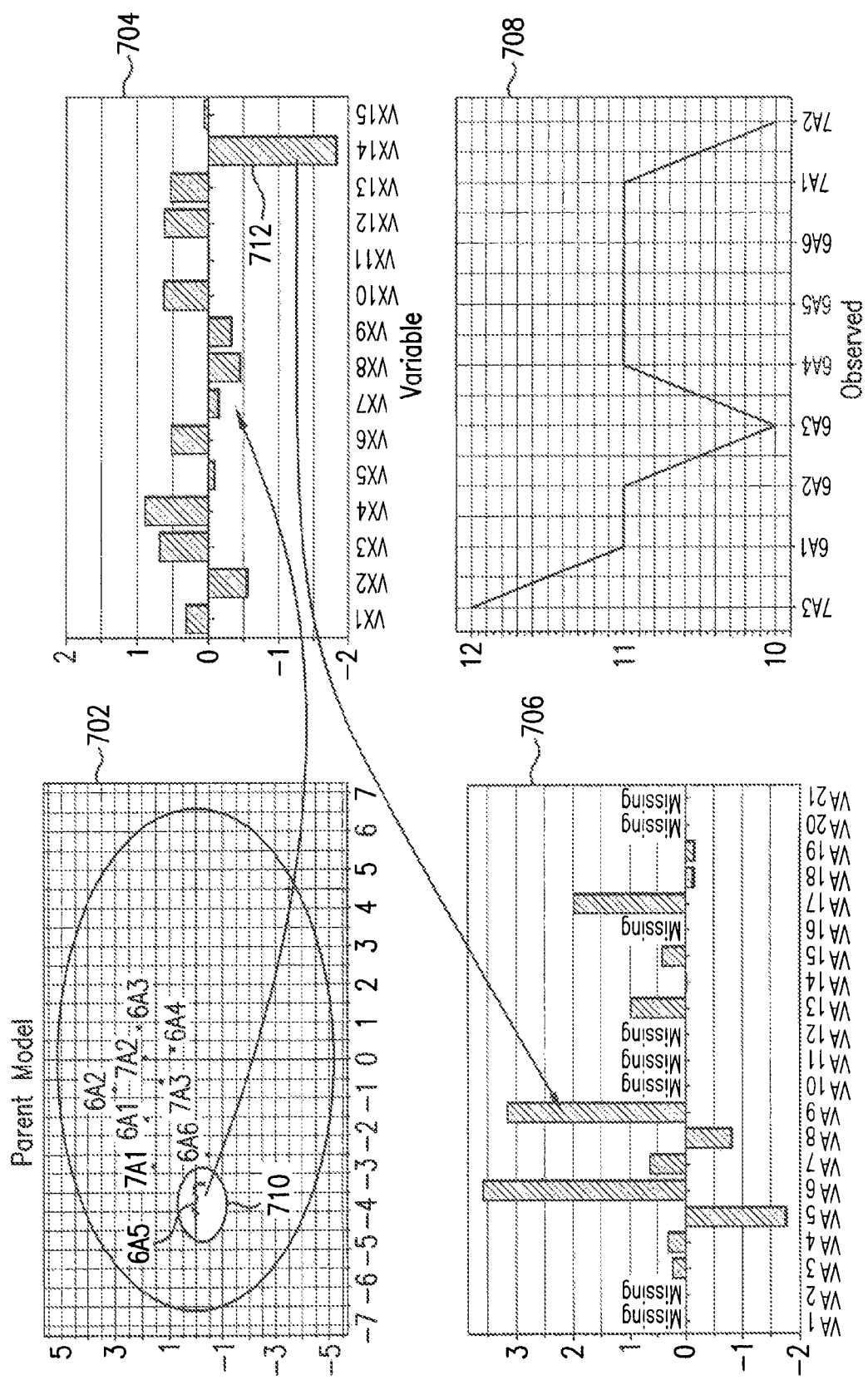
FIG. 7 illustrates the application of a hierarchical model according to an embodiment of the present invention to process and present chromatography data.

FIG. 7 illustrates the application of a hierarchical model according to an embodiment of the present invention to process and present chromatography data. In particular, FIG. 7 illustrates the graphical output of an example system according to an embodiment of the present invention (plots 702, 704, and 706) compared to the output of a conventional pulse test HETP system (plot 708). For example, the graphical output can be generated using a graphical module such as multivariate graphical module 404, described above in FIG. 4.

Plot 702 is a parent PCA plot constructed according to a hierarchical model according to an embodiment of the present invention. Each data point in plot 702 corresponds to a respective batch in the process. A shown in plot 702, an atypical batch appears as an outlier data point such as data point 710. According to an embodiment of the invention, a user may examine the causes for an outlier data point in the parent PCA plot by observing its sub-model components. For example, as shown in FIG. 7, the user may view a histogram plot 704 that shows the sub-model components of outlier data point 710. The user can then determine which sub-model may be out of trend (i.e., "drill down" into the model to identify which sub-model is out of trend). In addition, according to an embodiment of the invention, the user may further determine why a particular sub-model may be out of trend by further examining its component parameters. For example, as shown in FIG. 7, the user can view a histogram plot 706 that shows the parameter components of histogram bar 712. This allows the user to determine the one or more parameters that may have abnormal values.

In contrast, plot 708 shows the output of a conventional pulse test HETP. As shown, the univariate view of plot 708 fails to show any trend in the data and is thus significantly inferior to graphical outputs according to embodiments of the present invention.

FIGS. 8-14 to be described below illustrate various column monitoring capabilities of an example system for evaluating chromatography column performance according to an embodiment of the present invention. The example system uses one or more of the data analysis methods described above and a hierarchical data model according to an embodiment of the present invention. In particular, the hierarchical model was constructed using the parameters shown below in Table 1, based on 15 batches of data.

TABLE 1

| PARAMETER | SOURCE |
| --- | --- |
| Gaussian HETP | Transition Analysis |
| Non-Gaussian HETP | Transition Analysis |
| Non-Gaussian N | Transition Analysis |
| Non-Gaussian tau | Transition Analysis |
| Asymmetry | Transition Analysis |
| CDM tau | Transition Analysis |
| Peclet Number | Transition Analysis |
| CDM Mean Square Errors | Discoverant |
| Effluent Osmolality | Discoverant |
| Effluent pH | Discoverant |
| Step Yield | Discoverant |

Further, in order to ensure that the model was sensitive and not subject to noise, each column was modeled separately. Models were constructed based on 15 "good" batches of data, and known failures were modeled to show up as outliers in the model. The models, when applied to rProteinA, TMAE or phenyl columns on a commercial process were able to detect drifts in performance over the lifetime of a column, detect atypical instrument performance, detect difference in elution conditions, empirically judge the suitability of a repack, detect product related impurities and detect process related impurities. Applications such as these are exemplified in the Figures and discussion provided herein.

Figure 8:
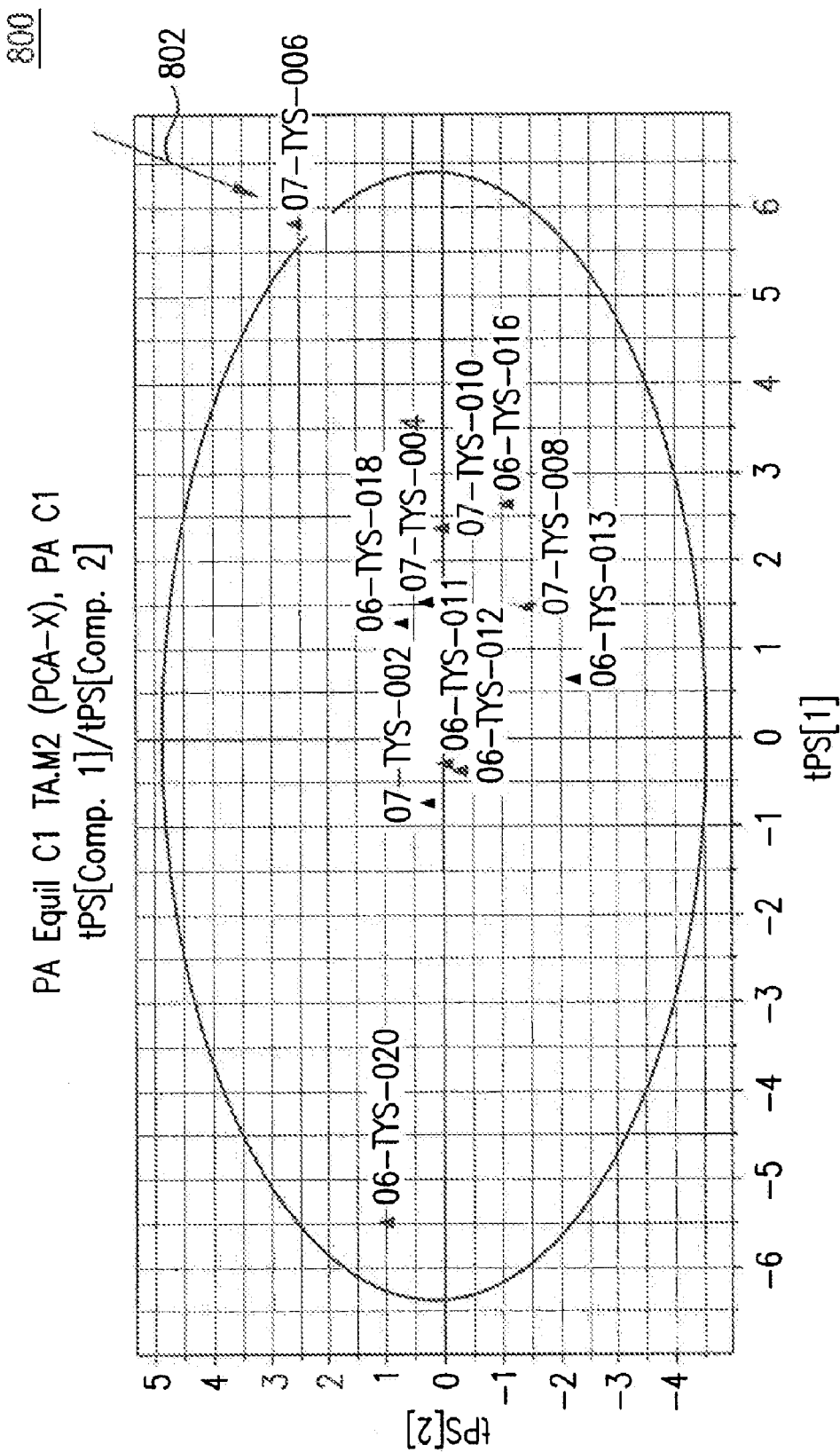
FIGS. 8-14 illustrate various column monitoring capabilities of an example system for evaluating chromatography column performance according to an embodiment of the present invention.
Figure 9:
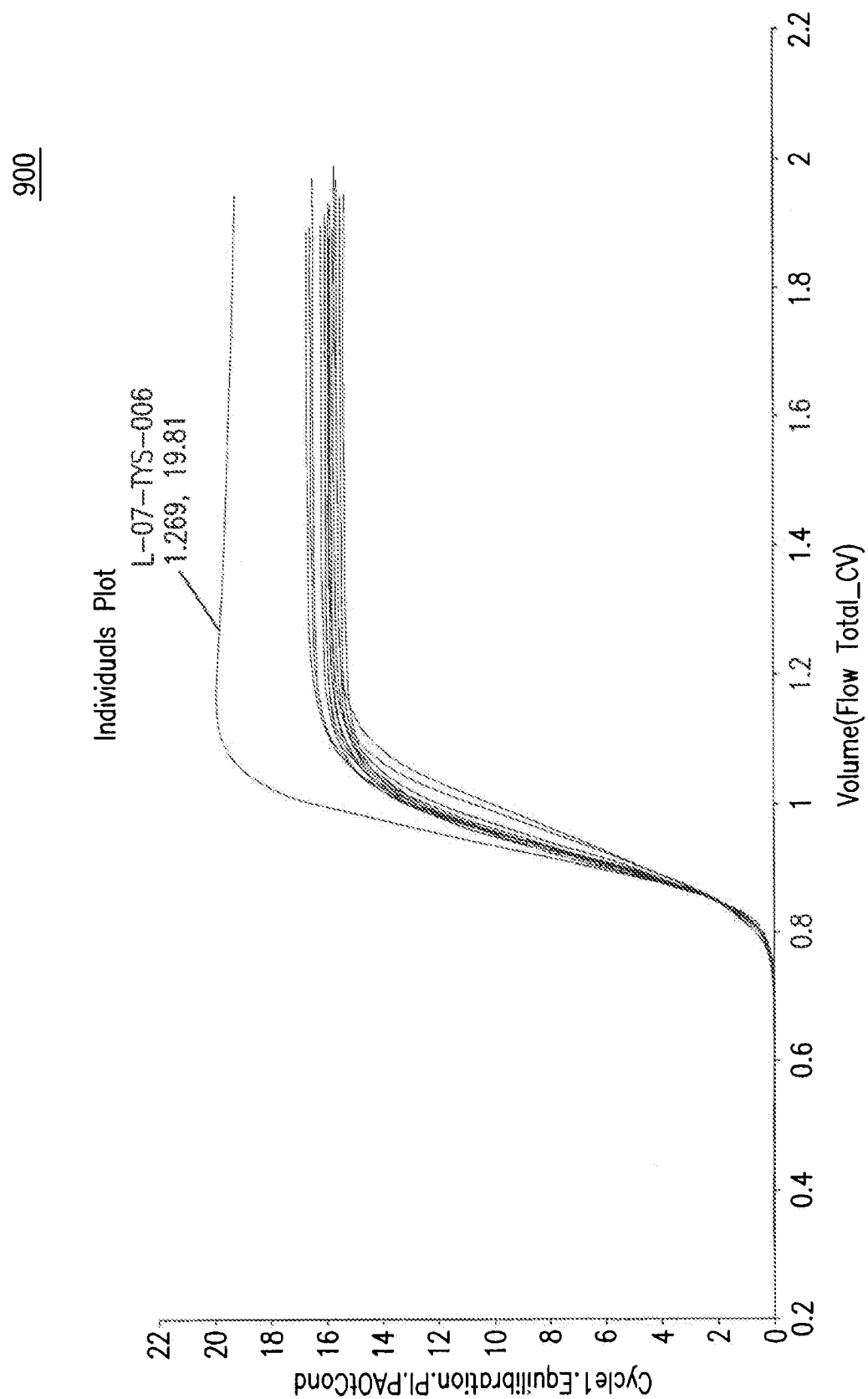

FIGS. 8 and 9 illustrate the example system's capability to detect mechanical issues. In particular, FIG. 8 illustrates a PCA plot 800 of the model for a rProtein A column. As batches are received, input parameters are added into the model, and a multivariate comparison is performed on all parameters to isolate differences between observations. Note that since PCA plot 800 is for a single column, it would correspond to a sub-model in the context of the hierarchical model described above. As shown in FIG. 8, the sub-model for the rProtein A column shows that the observations (batches) are well distributed within a 95% confidence ellipse, with the exception of one batch that corresponds to outlier data point 802.

As described above, according to an embodiment of the invention, the model provides the ability to determine which parameter(s) is causing an outlier data point in the PCA plot. In this example, it was determined upon further examination that conductivity in the outlier batch was 3 standard deviations (SD) away from its historical mean. To check this finding, univariate trends of conductivity during elution for the outlier batch were overlayed with other batches as shown in FIG. 9. This confirmed the differences between the outlier batch and the other batches. Subsequently, upon investigation, it was determined that the conductivity meter was faulty and had to be replaced. Typically, detecting an event such as this one is relatively difficult due to the complexity of the data analysis involved. Indeed, to detect this kind of event, the data management system would need to have the ability to perform pattern recognition. However, as described above, the event was detected fairly easily using embodiments of the present invention. This further demonstrates the utility of the multivariate model in processing a large volume of information and isolating batch-to-batch differences without necessarily having to parse through a multitude of univariate parameters.

Figure 10:
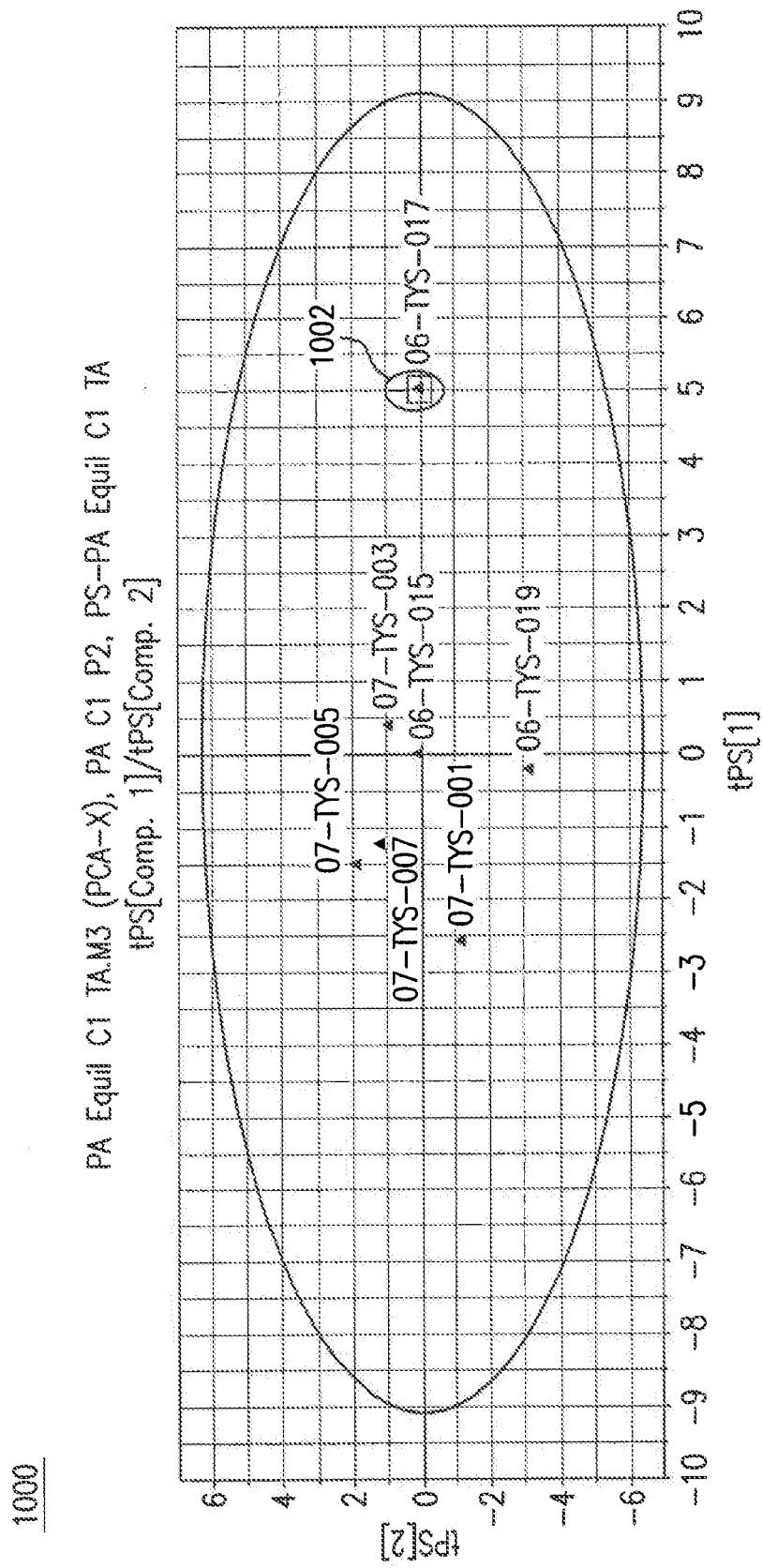
Figure 11:
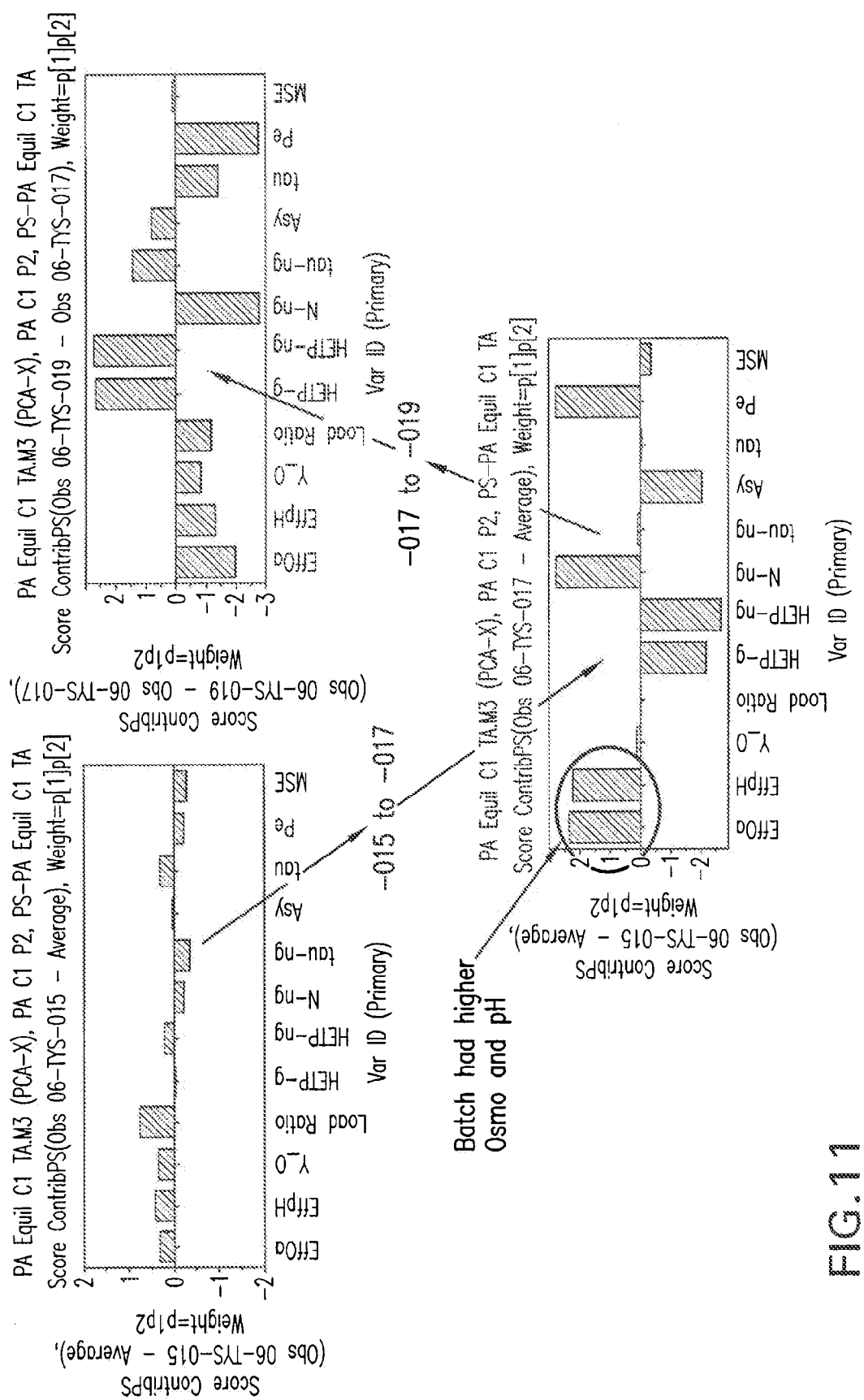

FIGS. 10 and 11 illustrate the example system's capability to determine differences in elution conditions between batches. For example, in FIG. 10, an outlier batch is detected when its corresponding data point appears as an outlier data point 1002 on PCA plot 1000. Subsequently, upon further examination as shown in FIG. 11, it is determined that the osmolalities of the batch are significantly higher than for other batches. This observation explained a difference in yield for this batch compared to historical values. It is noted that while traditional analysis methods generally focus on yields and upon detecting a lower yield examine input parameters to identify batch differences, embodiments of the present invention examine inputs in a multivariate fashion to identify variances before they manifest themselves in terms of outputs. As such, embodiments of the present invention results in faster detection of batch differences.

Figure 12:
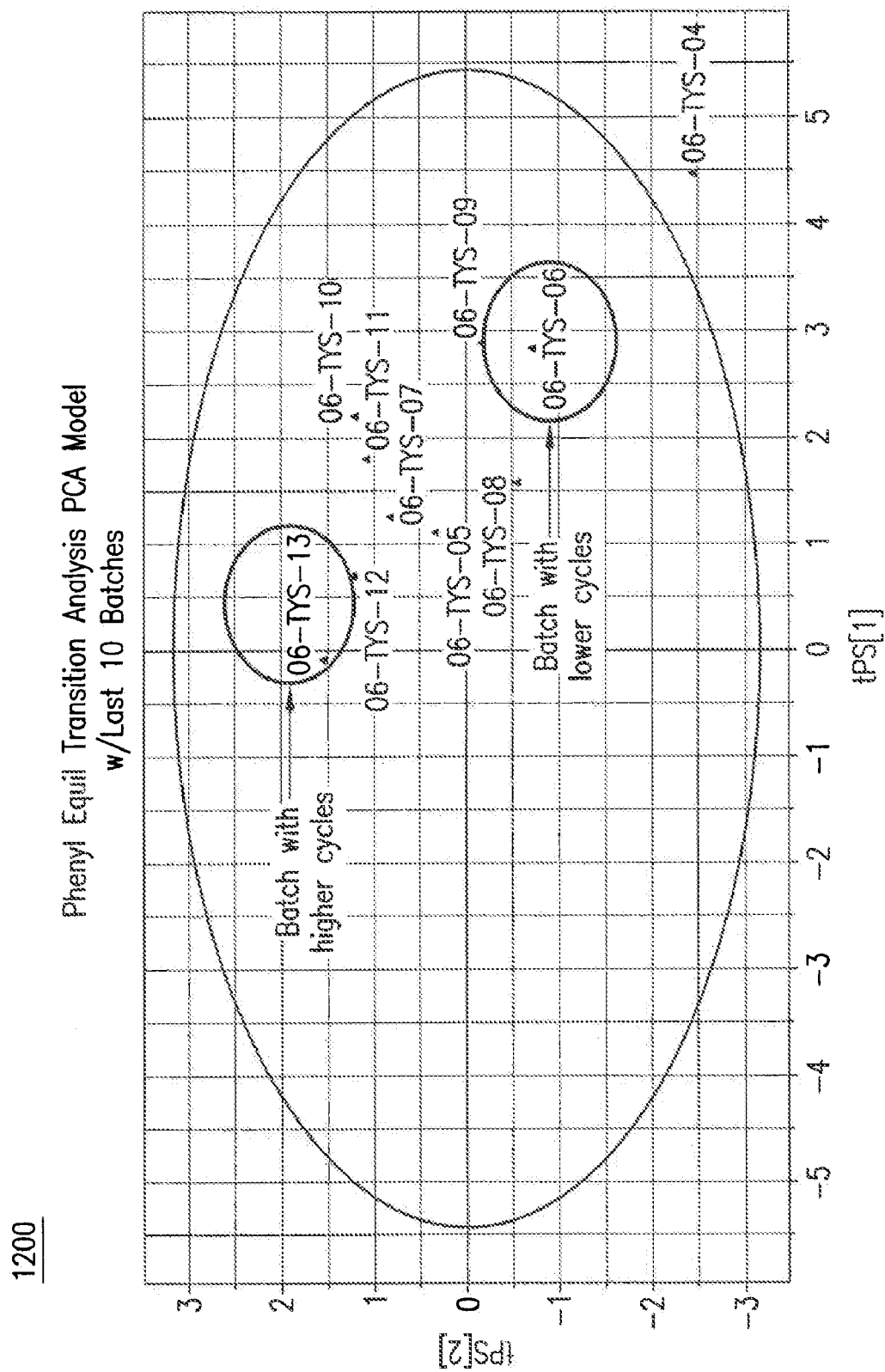
Figure 13:
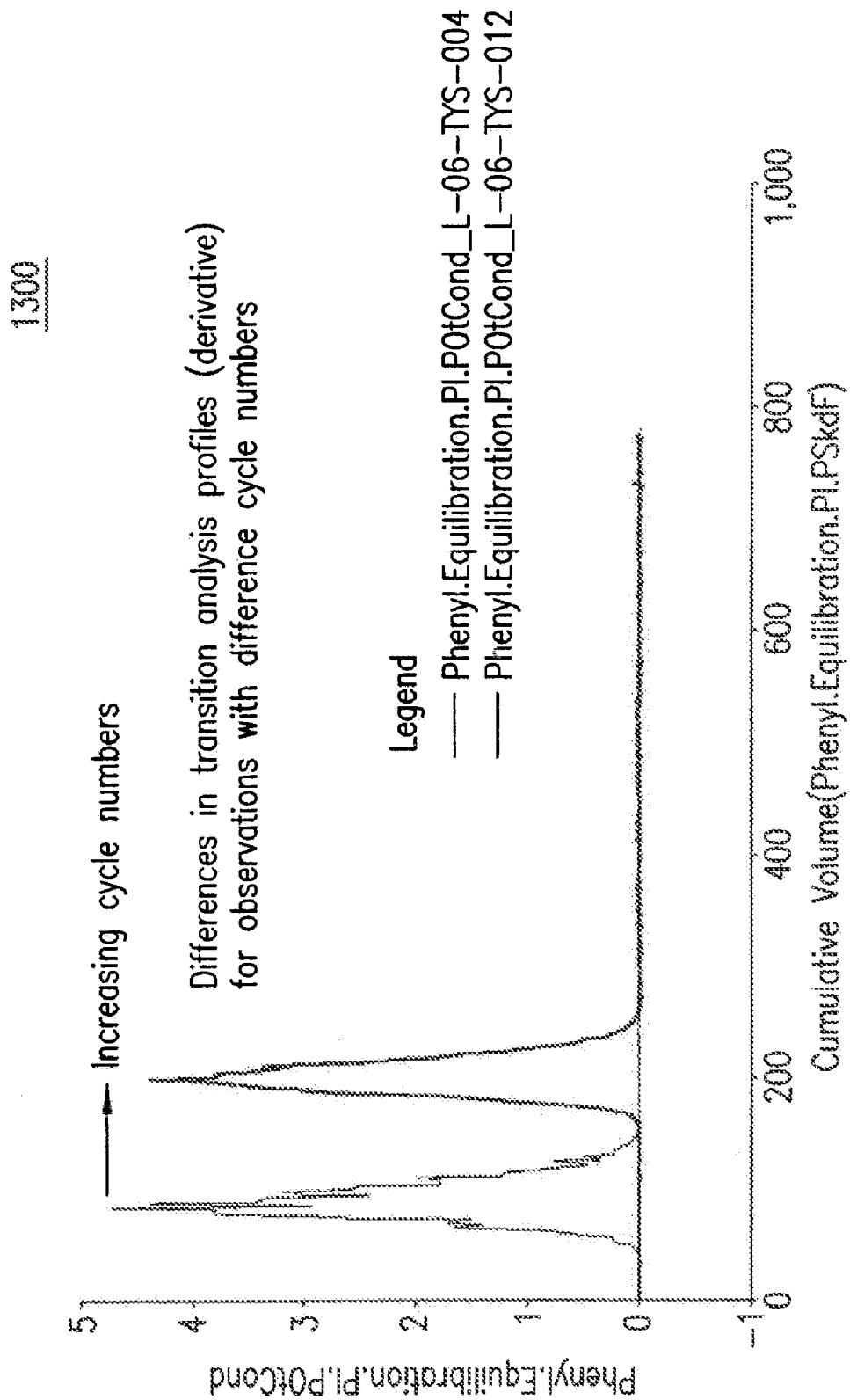

FIGS. 12 and 13 illustrate the example system's capability to detect subtle and gradual changes in performance over time. In particular, FIG. 12 is a PCA plot with data corresponding to the last ten batches in a process. As shown in FIG. 12, data points corresponding to batches with lower cycles can be readily distinguished from data points corresponding to batches with higher cycles. As such, performance variations over time can be easily detected.

Alternatively, according to an embodiment of the present invention, PLS methods can be used, wherein a parameter of interest (e.g., chromatogram characteristics, step yields, transition analysis parameters, etc.) can be set as the Y vector in the PLS regression. As such, parameter observations will result in a distribution that reflects the impact of the varying inputs on the observations. One advantage of this approach is that column lifetime can be determined based on an empirical examination of time variations of parameters within the column, as opposed to based on variations in output. As such, for example, decisions regarding re-packed columns can be made in advance of issues/abnormalities appearing in the output. As an example, a model according to an embodiment of the present invention was applied to a Phenyl column over its last 20 cycles, with the parameter of interest being the transition analysis profile. As shown in FIG. 13, transition analysis profiles for observations with different cycle numbers resulted in a distribution that is aligned with cycle number progression. Upon further analysis, it was determined that there was a slight shift in transition analysis parameters (non-Gaussian HETP in this case), which over time was increasing as the cycle number approached column lifetime end.

Figure 14:
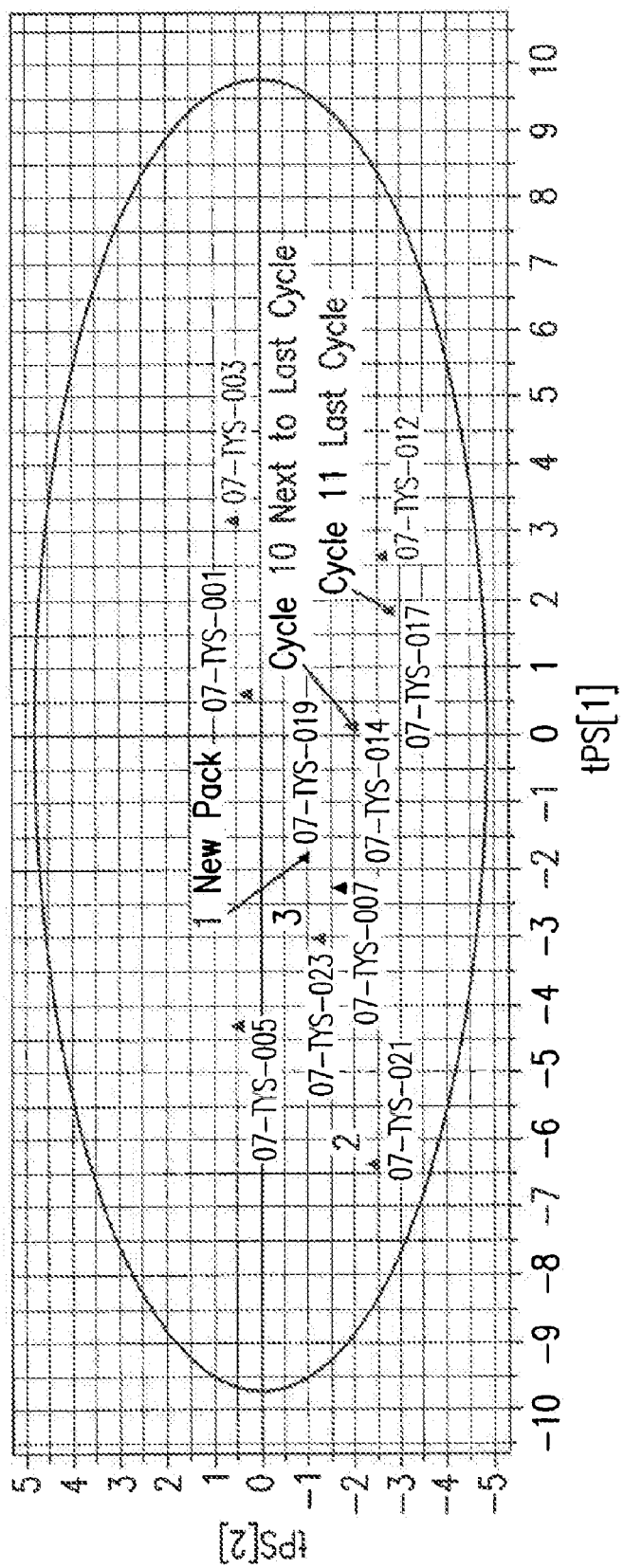

Multivariate models according to embodiments of the present invention can also be used to determine the quality of a re-packed column. In an embodiment of the invention, this can be done by determining whether the re-packed column conforms to an established process signature. As an example, this was applied to a Phenyl column as illustrated in FIG. 14. As shown in FIG. 14, it was observed that a multivariate view of 15 key chromatography parameters placed a data point corresponding to the first batch from the re-packed column in the center of PCA plot 1400. This confirmed that the re-packed column was performing similarly to the old column in its early cycles.

Embodiments of the invention includes application of the methods described herein to any type of chromatography method. Such chromatography methods include, for example but without limitation: gas chromatography, liquid chromatography (e.g., high performance liquid chromatography); affinity chromatography; supercritical fluid chromatography; ion exchange chromatography; size-exclusion chromatography; reversed phase chromatography; two-dimensional chromatography; fast protein (FPLC) chromatography; countercurrent chromatography; chiral chromatography; aqueous normal phase (ANP) chromatography; mixed mode chromatography; pseudo-affinity chromatography; etc.

Embodiments of the invention includes application of the methods described herein in the use of chromatography methods for isolation of macro- and micro-biological and pharmacological compounds. Such compounds may include, for example but without limitation: proteins (including, for example, antibodies and fragments thereof); nucleic acids; carbohydrates; lipids; organic small molecules; non-organic small molecules; viruses; liposomes; and hybrids or variant forms of any such compounds.

Embodiments of the invention includes a graphical display of the performance data values generated by multivariate analysis of transition and/or process data. For example, a graphical display of performance data may be presented on a computer monitor. The graphical display can include an interactive user interface that enables a user to select particular performance data values for observation and analysis. The interactive user interface can provide an efficient way of quantitatively displaying differences between observations, while at the same time allowing a user to investigate and reveal potential causes of variation between observations by progressively narrowing down the root cause of aberrant performance values.

Embodiments of the invention includes multivariate analysis of transition and/or process data for use in determining when to change or repack chromatography media.

Embodiments of the invention includes multivariate analysis of transition and/or process data for use in predicting when to change or repack chromatography media.

Embodiments of the invention includes multivariate analysis of transition and/or process data for use in identifying the source of unacceptable chromatography performance.

Embodiments of the invention includes making a determination that the quality of the chromatography performance is unacceptable if one or more performance parameters are outside a specified range of values. In one embodiment, an automated alert system is triggered to notify users of the determination.

EXAMPLES

Example 1

Detecting Upward Trend in Host Cell Protein Contamination

Figure 15:
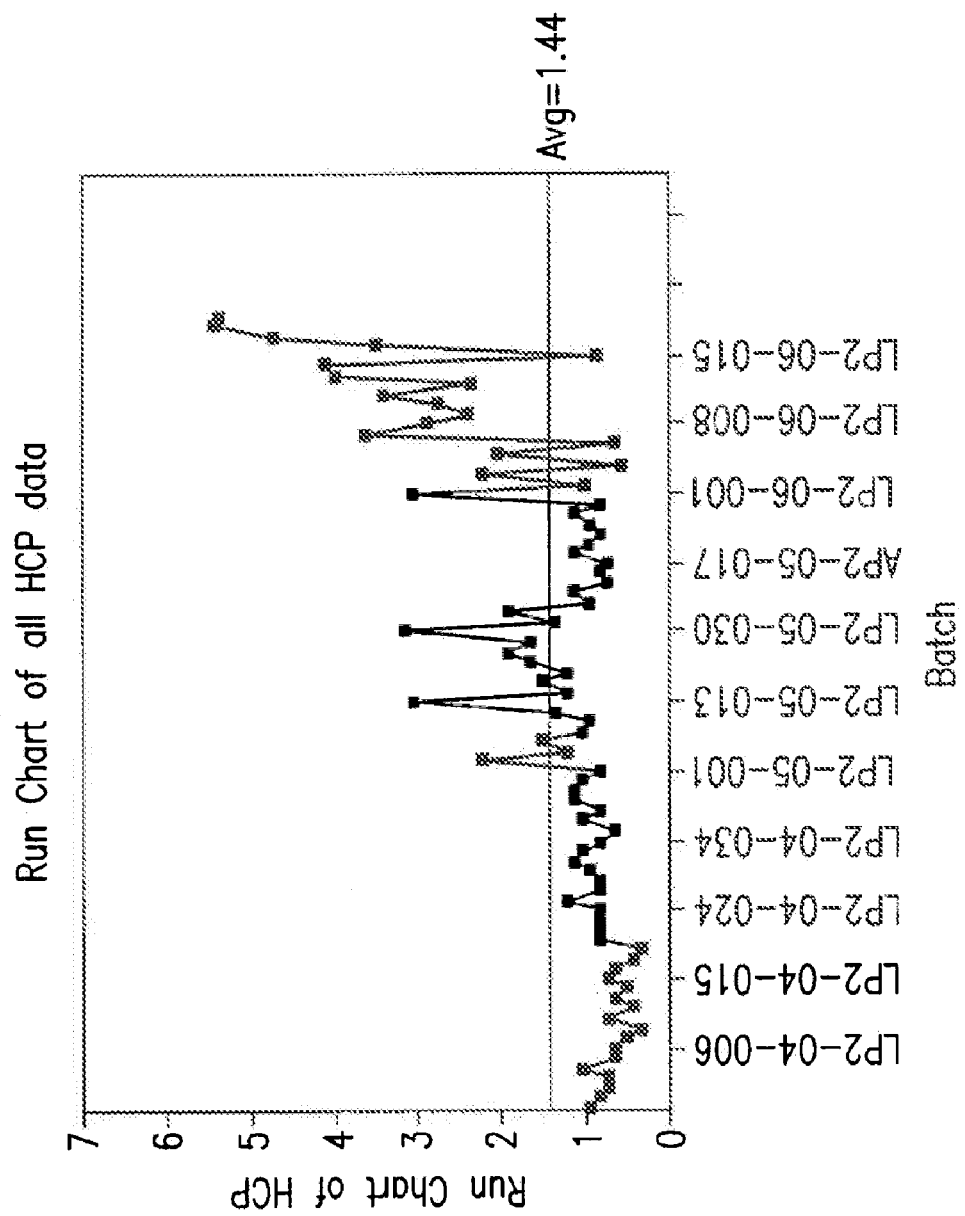
FIG. 15 illustrates the increasing content of host cell protein (HCP) present (Y-axis; relative units) from successive column chromatography procedures (a.k.a., column "runs" or "batches") (X-axis).

During preparative scale production of a protein (via multiple and separate column chromatography "runs") an upward trend in mammalian-Host Cell Protein (HCP) contamination was observed (FIG. 15). The cause of the increased contamination, however, was not readily apparent based on univariate analysis of the available parameters. An initial hypothesis was that increased HCP levels was being caused by increased overall product output (i.e., increased product titer). Investigation revealed, however, that this could not be the sole root cause because chromatography runs with lower product titers were displaying similar upward HCP trends. Further compounding identification of the cause was the fact that batches were being produced in two separate units (Unit 1 and Unit 2) and higher titer batches were being produced in Unit 1 because a new cell bank was being used in this particular unit. Thus, decoupling the increasing HCP trend based on differences in cell cultures or based on deviation in the purification process was a highly complicated because of the numerous variables in these processes.

In attempt to identify the cause of increasing HCP, one-way analysis was performed for all HCP data by separating the data based on high versus low product titer batches and by seperating data based on purification by Unit 1 versus purification by Unit 2. The one-way platform analyzes how the distribution of a continuous Y variable (in this case HCP content) differs across groups (e.g., higher titer versus lower titer preparations and Unit 1 versus Unit 2 preparations) defined by a categorical x variable (batches). Another approach (using the same analysis) to compare the two means of the data sets is to determine if actual differences are greater than their least significant difference (LSD). This least significant difference is a Student's t-statistic multiplied by the standard error of the difference of the two means. The one-way analysis showed that higher titer batches had a significantly higher mean HCP content than lower titer batches (2.87 vs 1.06, respectively). In addition, it was also observed that Unit 1 and Unit 2 had significantly different mean HCP contents (1.46 vs 0.85, respectively). However, this did not decouple the differences in purification units from the impact of high versus low titers. Thus, to identify the root cause, it was decided to apply the multivariate model for analysis.

Figure 16:
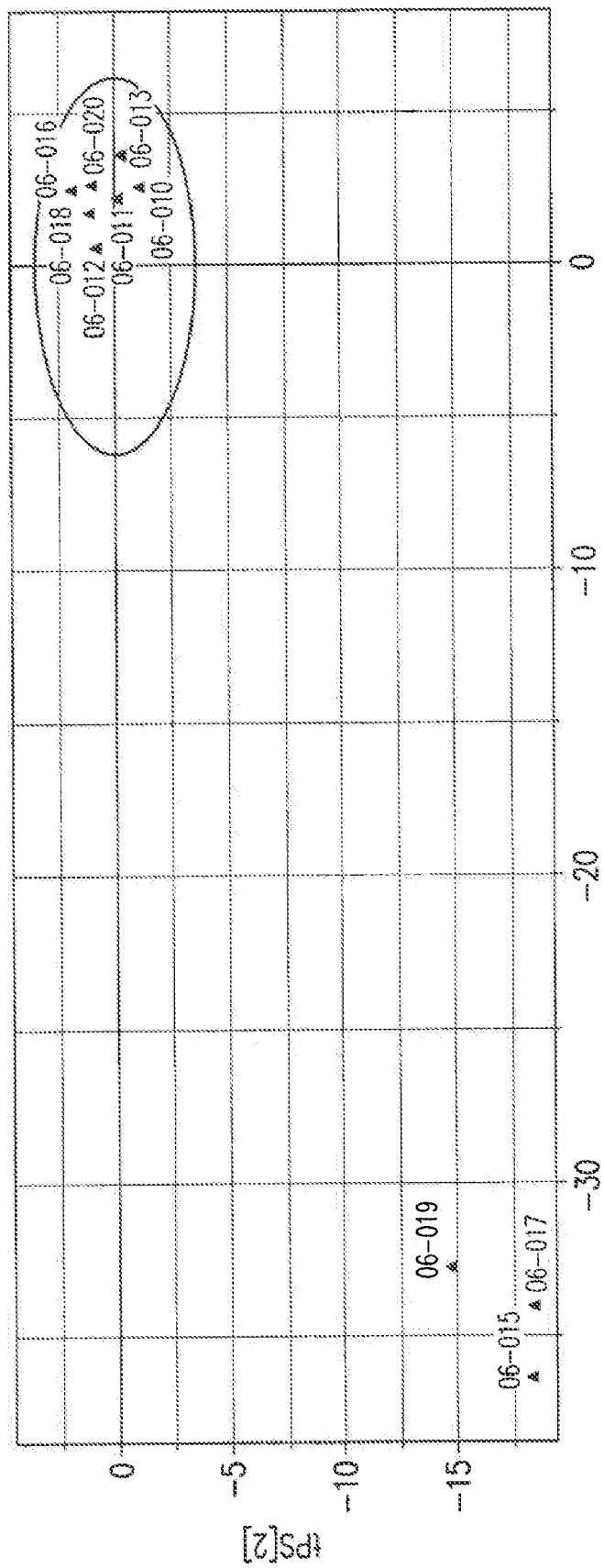
FIG. 16 shows PCA analysis utilized to depict column differences between purification Unit 1 and purification Unit 2.

Using the multivariate model, based on cell culture and purification sub-models, it was determined that the TMAE chromatography sub-model had the highest impact (or was the most significant sub-model) contributing to variation in HCP levels. (TMAE=Trimethylaminoethyl (a quarternary ammonia residue used in adsorption chromatography.)) Upon analyzing the PCA plot for the TMAE purification sub-model, it was clear there was a stark difference between observations in purification Unit 1 versus Unit 2 (FIG. 16).

Figure 17:
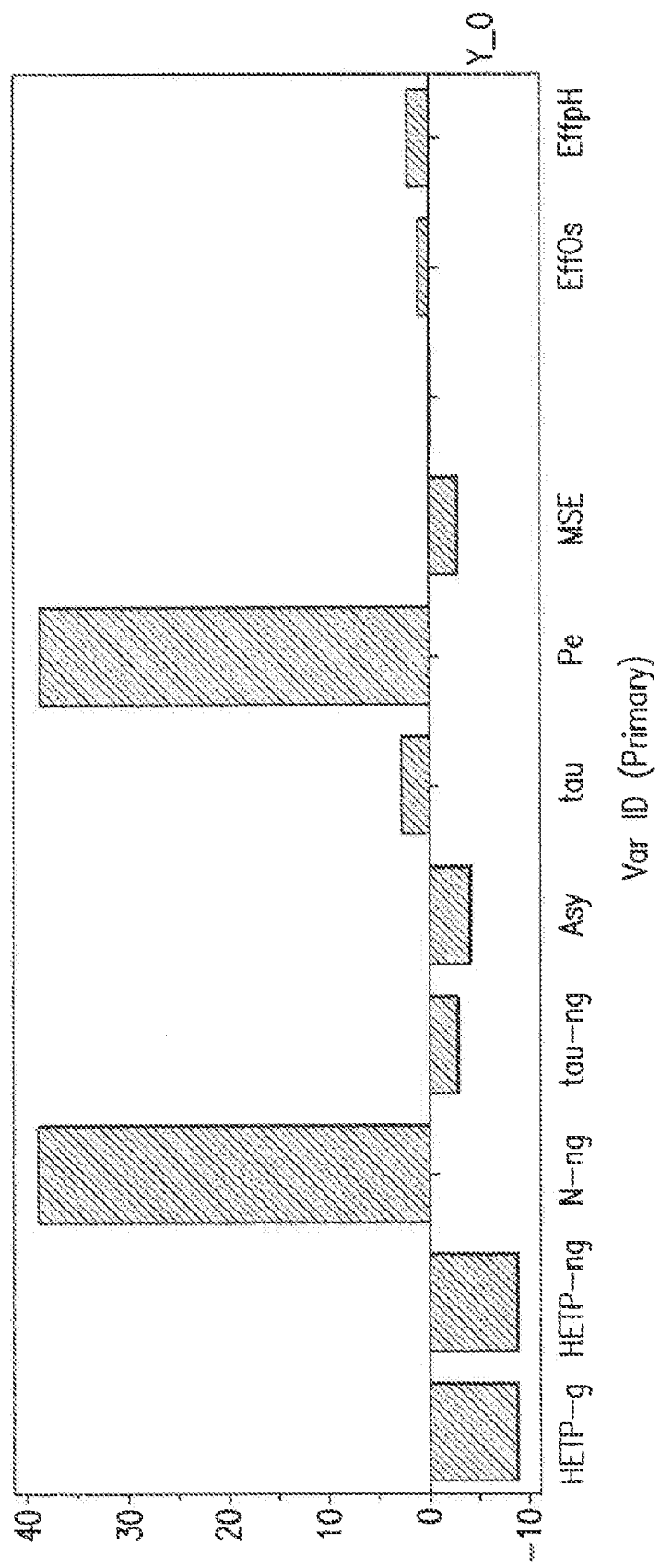
FIG. 17 shows Gap Analysis showing Transition Analysis HETP out of standard deviation (SD) control limits.

A review of the gap analysis in the TMAE sub-model confirmed that the value for the Non-Gaussian HETP for the columns in the two purification units were significantly different (FIG. 17). Additionally, when chromatography elution profiles from both purification units were overlayed, the differences in TMAE column performance was further confirmed (FIG. 18).

While the above-described analysis confirmed that the TMAE columns in different purification units were performing differently, it still needed to be ascertained that the differences in performance was in fact contributing to differences in HCP content. Accordingly, multivariate analysis was conducted on 62 in-process variables, using HCP content as the vector of interest. A model was created for explaining the variation in HCP based on the available data. The multivariate model revealed that the 2 VIPs (variable of importance in the projection) that were ranked highest in the model were associated with the TMAE cycle count. The VIPs give the relative importance of each principal component (PC) contributing to the model, and PCs with higher VIP scores are more relevant to the model. As such, in this case, the TMAE cycle count was seen to have the highest impact on the upward trend in NSO-HCP. To further confirm that the developed model was valid, the results of residuals ($R^2$ and $Q^2$) were used to confirm applicability of the analysis. $R^2$ provides a measure of how well the model describes a given variable, and $Q^2$ measures the predictive power of the model. In the biologics industry, $Q^2$ values of about 0.4 and higher are considered indicative of highly valid models. For this particular analysis, the value of $Q^2$ associated with the multivariate model developed was 0.827, which shows excellent predictability. A response surface plot for HCP, TMAE cycle count and offline pH on day 3 (which was also determined to be an important variable in the multivariate analysis) further confirmed that the correlation was strongest between increased HCP content and column cycle number (data not shown). It was evident that the TMAE column in purification Unit 1 was not performing optimally when the value of non-gaussian HETP was plotted against TMAE cycle number (data not shown).

Thus, based on the multivariate analysis it was determined to repack the column with new resin. The multivariate model confirmed that after the re-pack the TMAE column performance in purification Unit 1 was different from historical Unit 1 column runs, but was now closer in performance to that in purification Unit 2 (FIGS. 18 & 19). Indeed, the repack resulted in significantly reduced HCP content (FIG. 20). Thus, by applying the principles described herein multivariate analysis was used to identify, and thereby rectify, the root cause of an undesirable trend in chromatography performance.

Example 2

Analyzing Causes of Process Related Impurities

Analysis of the host cell protein (HCP) concentration in the final Drug Substance (DS) showed a substantial variation over a number of manufacturing batches (HCP at 0.5 to 7.9 ppm). The main suspect of the root cause analysis pointed towards an Anion Exchange Chromatography (AIEX) step in the purification procedures with the main hypothesis being that the performance of the step declined with repeated use of the stationary phase (i.e., AIEX media). In order to test this hypothesis, continuous traces of the UV absorption at 280 nm as well as conductivity traces were analyzed. The goal was to build a multivariate process model and correlate a quantitative analysis of the continuous data to off-line quality attribute tests. An MVA model was built with an initial set of 58 process variables. After ranking the most important variables, a reduced model with 14 parameters extracted from the UV traces of the AIEX chromatogram was obtained. This was further reduced to a model with 8 important parameters for predicting the levels of host cell protein in the Drug Substance. FIG. 21 shows the resulting parameter set. A model of excellent fit and predictability was obtained as evidenced by R2 and Q2 values of 0.76 and 0.73, respectively. FIG. 22 shows the excellent correlation between measured and predicted HCP concentrations in the DS. Thus, it was confirmed that variations in HCP content were the result of reduced performance of the AIEX step over a large number of use cycles.

Example 3

Analyzing Causes of Product Related Impurities

The concentration of a product related impurity was observed to increase over a number of manufacturing batches (0.9 to 1.9%). Investigation revealed two main suspects: 1) a potential variation of the impurity introduced by cell culture conditions; and, 2) deteriorated packing of the hydrophiboc interaction chromatography (HIC) step responsible for removing the impurity.

Continuous signals from multiple chromatograms across different cell culture batches and multiple column packings were analyzed using UV absorption at 280 nm and by analyzing conductivity signals. The goal, then, was to build a multivariate process model and correlate continuous data to off-line quality attribute tests. The resulting PCA model used 25 parameters; 17 parameters stemming from analysis of UV traces, 7 parameters resulting from an analysis of conductivity traces, and 1 parameter from the number of successive uses of the stationary phase (i.e., the 25th and final parameter). A model of respectable accuracy was obtained, represented by R2 and Q2 of 0.4 and 0.5, respectively.

FIG. 23 shows a PCA plot of the resulting model. The ellipsoid represents the 95% confidence interval, while the curved arrow indicates how the predicted and measured impurity concentration trends with repeated use. Thus, use of these tools permitted to differentiate between the impact of HIC column packing quality on the separation efficiency of the chromatography step and cell culture variability as a contributor to the impurity load of the chromatography step.

In sum, these examples demonstrate the utility and applicability of a multivariate analytical approach to column chromatography monitoring, particularly in conjunction with the analytical "toolbox" described herein. Without the application of this methodology, it would have been very difficult (from an empirical standpoint) to determine what stage of the preparation and purification process was responsible for unacceptable deviations in the purification procedures. Hence, the examples provided herein demonstrate, among other things, that:

Use of hierarchical parent models allows process operators to identify a sub-model or sub-models of critical interest;
  Use of transition analysis as part of multivariate model analysis permits application of sensitive analytics to identify compromised column performance;
  Use of multivariate methods permits isolation of differences between performance of entirely separate columns;
  Use of a multivariate model analysis allows isolation and identification of the cause of decreased performance resulting from gradual column degradation (e.g., resulting from increasing numbers of column cycles);
  Multivariate model analysis permits efficient analysis of column repack results; and,
  Multivariate model analysis permits efficient detection of root causes for process and product related impurities.

Hence, these examples demonstrate that application of multivariate analysis methods using transition analysis data from chromatography steps provides an efficient and comprehensive means of evaluating column performance. By using multiple transition analysis calculations in multivariate analysis, a substantial amount of information about column performance can be combined and presented in a compact form, thereby providing a robust tool for evaluating chromatography performance. Thus, as opposed to merely observing univariate trends, the use of transition analysis parameters in a multivariate form can be used, for example, to detect column lifetimes by computing a signature of an "acceptable model resin" and tracking the actual performance of a column against the established signature. Moreover, the methods described herein provide, inter alia, a multivariate toolbox of analytics that can be used to determine performance signatures of columns within a purification process.

The foregoing description of the specific embodiments will so fully reveal the general nature of the invention that others can, by applying knowledge within the skill of the art, readily modify and/or adapt for various applications such specific embodiments, without undue experimentation, and without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

It is to be noted that while many of the examples features described herein have made references to chromatography step-up transitions, the present invention works equally well for both step-up and step-down transition. Furthermore, the present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The breadth and scope of the present invention should not be limited by any of the above-described exemplary embodiments, but should be defined only in accordance with the following claims and their equivalents. In addition, it is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

What is claimed is:

1. A method for operating a chromatography column, comprising:
  a) monitoring an output of said chromatography column to generate a plurality of process data values corresponding to respective output observations;
  b) performing transition analysis on said plurality of process data values to generate a plurality of transition data values;
  c) applying one or more multivariate statistical analysis methods on said process data values and transition data values according to a hierarchical model, to generate a plurality of performance values that correspond to said output observations;
  d) graphically displaying said performance data values; and
  e) replacing or repackaging the chromatography column.

2. The method of claim 1, wherein the monitored output comprises a parameter selected from the group consisting of:
  a) conductivity;
  b) pH;
  c) salt concentration;
  d) light absorption;
  e) fluorescence after excitation with light of a suitable wavelength;
  f) refractive index;
  g) electrochemical response; and
  h) mass spectrometry data.

3. The method of claim 1, further comprising making a determination that the chromatography performance is unacceptable if a performance value calculated in (d) is outside a specified range of values.

4. The method of claim 3, wherein said determination triggers an automated alert system to notify users of said determination.

5. The method of claim 1, further comprising making a determination that the chromatography performance is acceptable if a performance value calculated in (d) is inside a specified range of values.

6. The method of claim 1, wherein the chromatography column performance is monitored during separation of a biomolecule or pharmacologic compound.

7. The method of claim 6, wherein said biomolecule or pharmacologic compound is selected from the group consisting of:
  a) a protein;
  b) a nucleic acid;
  c) a carbohydrate;
  d) a lipid;
  e) a pharmacologically active small molecule; and
  f) a hybrid or variant form of any one of a) through e).

8. The method of claim 1, wherein the chromatography method performed is selected from the group consisting of:
   a) gas chromatography;
   b) liquid chromatography;
   c) affinity chromatography;
   d) supercritical fluid chromatography;
   e) ion exchange chromatography;
   f) size-exclusion chromatography;
   g) reversed phase chromatography;
   h) two-dimensional chromatography;
   i) fast protein (FPLC) chromatography;
   j) countercurrent chromatography;
   k) chiral chromatography;
   l) aqueous normal phase (ANP) chromatography;
   m) mixed mode chromatography; and
   n) pseudo-affinity chromatography.

9. A graphical display of the performance data values generated by the method of claim 1.

10. The graphical display of claim 9, wherein the display is a computer monitor.

11. The method of claim 1, wherein said monitoring further comprises identifying the source of unacceptable chromatography performance.

12. The method of claim 1, wherein said monitoring comprises use of a statistical analysis method selected from the group consisting of:
   a) Principal Component Analysis (PCA);
   b) Partial Least Squares (PLS); and
   c) Least Significant Difference (LSD).

13. The method of claim 1, further comprising:
   a) generating a plurality of chromatograms corresponding to said respective output observations;
   b) overlaying said plurality of chromatograms on top of each other; and
   c) applying pattern recognition methods to determine differences in column performance based on said plurality of chromatograms.

14. The method of claim 1, further comprising:
   a) generating a plurality of chromatograms corresponding to said respective output observations;
   b) generating an ideal chromatography standard; and
   c) comparing said plurality of chromatograms to said ideal chromatography standard to detect atypical column behavior.

* * * * *